(12) United States Patent
Libbus et al.

(10) Patent No.: US 8,457,734 B2
(45) Date of Patent: Jun. 4, 2013

(54) SYSTEM AND METHOD FOR NEURAL STIMULATION

(75) Inventors: Imad Libbus, St. Paul, MN (US); Andrew P. Kramer, Stillwater, MN (US); Anthony V. Caparso, St. Louis Park, MN (US); Kristofer J. James, Eagan, MN (US); Stephen Ruble, Lino Lakes, MN (US); Weiying Zhao, Blaine, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1158 days.

(21) Appl. No.: 11/468,135

(22) Filed: Aug. 29, 2006

(65) Prior Publication Data
US 2008/0058871 A1    Mar. 6, 2008

(51) Int. Cl.
*A61N 1/365* (2006.01)

(52) U.S. Cl.
USPC ....... 607/2; 607/9; 607/11; 607/118; 607/119

(58) Field of Classification Search
USPC .................... 607/72, 74, 2, 9, 11, 118–119
See application file for complete search history.

(56) References Cited

U.S. PATENT DOCUMENTS

| | | | |
|---|---|---|---|
| 4,702,254 A * | 10/1987 | Zabara | 607/45 |
| 4,791,931 A | 12/1988 | Slate | |
| 5,097,833 A | 3/1992 | Campos | |
| 5,111,815 A | 5/1992 | Mower | |
| 5,154,172 A * | 10/1992 | Terry et al. | 607/64 |
| 5,190,035 A | 3/1993 | Salo et al. | |
| 5,199,428 A | 4/1993 | Obel et al. | |
| 5,203,326 A | 4/1993 | Collins | |
| 5,222,494 A | 6/1993 | Baker, Jr. | |
| 5,243,980 A * | 9/1993 | Mehra | 607/6 |
| 5,318,592 A | 6/1994 | Schaldach | |

(Continued)

FOREIGN PATENT DOCUMENTS

| EP | 0547734 A2 | 6/1993 |
|---|---|---|
| EP | 0688578 A1 | 12/1995 |

(Continued)

OTHER PUBLICATIONS

"U.S. Appl. No. 11/087,935, Notice of Allowance mailed Oct. 23, 2008", 6 pgs.

(Continued)

*Primary Examiner* — Joseph Stoklosa
(74) *Attorney, Agent, or Firm* — Schwegman Lundberg & Woessner, P.A.

(57) ABSTRACT

Various aspects provide an implantable device. In various embodiments, the device comprises at least one port, where each port is adapted to connect a lead with an electrode to the device. The device further includes a stimulation platform, including a sensing circuit connected to the at least one port to sense an intrinsic cardiac signal and a stimulation circuit connected to the at least one port via a stimulation channel to deliver a stimulation signal through the stimulation channel to the electrode. The stimulation circuit is adapted to deliver stimulation signals through the stimulation channel for both neural stimulation therapy and CRM therapy. The sensing and stimulation circuits are adapted to perform CRM functions. The device further includes a controller connected to the sensing circuit and the stimulation circuit to control the neural stimulation therapy and the CRM therapy. Other aspects and embodiments are provided herein.

12 Claims, 14 Drawing Sheets

U.S. PATENT DOCUMENTS

| | | | |
|---|---|---|---|
| 5,324,316 | A | 6/1994 | Schulman et al. |
| 5,330,507 | A | 7/1994 | Schwartz |
| 5,356,425 | A | 10/1994 | Bardy et al. |
| 5,411,531 | A | 5/1995 | Hill et al. |
| 5,437,285 | A | 8/1995 | Verrier et al. |
| 5,507,784 | A | 4/1996 | Hill et al. |
| 5,522,854 | A | 6/1996 | Ideker et al. |
| 5,540,730 | A | 7/1996 | Terry, Jr. et al. |
| 5,571,150 | A * | 11/1996 | Wernicke et al. ............... 607/72 |
| 5,578,061 | A | 11/1996 | Stroetmann et al. |
| 5,658,318 | A | 8/1997 | Stroetmann et al. |
| 5,690,681 | A | 11/1997 | Geddes et al. |
| 5,700,282 | A | 12/1997 | Zabara |
| 5,707,400 | A | 1/1998 | Terry, Jr. et al. |
| 5,916,239 | A | 6/1999 | Geddes et al. |
| 6,006,134 | A | 12/1999 | Hill et al. |
| 6,058,331 | A | 5/2000 | King |
| 6,073,048 | A | 6/2000 | Kieval et al. |
| 6,134,470 | A | 10/2000 | Hartlaub |
| 6,161,042 | A | 12/2000 | Hartley et al. |
| 6,164,284 | A | 12/2000 | Schulman et al. |
| 6,178,349 | B1 | 1/2001 | Kieval |
| 6,181,966 | B1 | 1/2001 | Nigam |
| 6,240,314 | B1 | 5/2001 | Plicchi et al. |
| 6,240,316 | B1 | 5/2001 | Richmond et al. |
| 6,272,377 | B1 | 8/2001 | Sweeney et al. |
| 6,285,907 | B1 | 9/2001 | Kramer et al. |
| 6,292,695 | B1 | 9/2001 | Webster, Jr. et al. |
| 6,371,922 | B1 | 4/2002 | Baumann et al. |
| 6,400,982 | B2 | 6/2002 | Sweeney et al. |
| 6,411,845 | B1 | 6/2002 | Mower |
| 6,415,183 | B1 | 7/2002 | Scheiner et al. |
| 6,421,557 | B1 | 7/2002 | Meyer |
| 6,449,507 | B1 | 9/2002 | Hill et al. |
| 6,473,644 | B1 | 10/2002 | Terry, Jr. et al. |
| 6,487,450 | B1 | 11/2002 | Chen |
| 6,493,585 | B2 | 12/2002 | Plicchi et al. |
| 6,511,500 | B1 | 1/2003 | Rahme |
| 6,516,227 | B1 | 2/2003 | Meadows et al. |
| 6,522,926 | B1 | 2/2003 | Kieval et al. |
| 6,532,388 | B1 | 3/2003 | Hill et al. |
| 6,542,774 | B2 | 4/2003 | Hill et al. |
| 6,564,096 | B2 | 5/2003 | Mest |
| 6,611,713 | B2 | 8/2003 | Schauerte |
| 6,622,041 | B2 | 9/2003 | Terry, Jr. et al. |
| 6,628,987 | B1 | 9/2003 | Hill et al. |
| 6,678,547 | B2 | 1/2004 | Carlson et al. |
| 6,748,272 | B2 | 6/2004 | Carlson et al. |
| 6,804,561 | B2 | 10/2004 | Stover |
| 7,069,070 | B2 | 6/2006 | Carlson et al. |
| 7,123,961 | B1 | 10/2006 | Kroll et al. |
| 7,155,284 | B1 | 12/2006 | Whitehurst et al. |
| 7,194,313 | B2 | 3/2007 | Libbus |
| 7,260,431 | B2 | 8/2007 | Libbus et al. |
| 7,277,761 | B2 | 10/2007 | Shelchuk |
| 7,317,948 | B1 | 1/2008 | King et al. |
| 7,493,161 | B2 | 2/2009 | Libbus et al. |
| 7,499,748 | B2 | 3/2009 | Moffitt et al. |
| 7,660,628 | B2 | 2/2010 | Libbus et al. |
| 7,801,604 | B2 | 9/2010 | Brockway et al. |
| 8,131,357 | B2 | 3/2012 | Bradley et al. |
| 8,155,756 | B2 | 4/2012 | Yang et al. |
| 2002/0026221 | A1 | 2/2002 | Hill et al. |
| 2002/0026222 | A1 | 2/2002 | Schauerte et al. |
| 2002/0042637 | A1 | 4/2002 | Stover |
| 2002/0058877 | A1 | 5/2002 | Baumann et al. |
| 2002/0107553 | A1 | 8/2002 | Hill et al. |
| 2002/0107557 | A1 | 8/2002 | Edell et al. |
| 2002/0116030 | A1 | 8/2002 | Rezai |
| 2002/0120304 | A1 | 8/2002 | Mest |
| 2002/0123769 | A1 | 9/2002 | Panken et al. |
| 2002/0143369 | A1 | 10/2002 | Hill et al. |
| 2002/0165586 | A1 | 11/2002 | Hill et al. |
| 2003/0003052 | A1 | 1/2003 | Hampton |
| 2003/0004549 | A1 | 1/2003 | Hill et al. |
| 2003/0023279 | A1 | 1/2003 | Spinelli et al. |
| 2003/0036773 | A1 | 2/2003 | Whitehurst et al. |
| 2003/0045909 | A1 | 3/2003 | Gross et al. |
| 2003/0060848 | A1 | 3/2003 | Keival et al. |
| 2003/0060857 | A1 | 3/2003 | Perrson et al. |
| 2003/0060858 | A1 | 3/2003 | Kieval et al. |
| 2003/0078623 | A1 | 4/2003 | Weinberg et al. |
| 2003/0078629 | A1 | 4/2003 | Chen |
| 2003/0100924 | A1 | 5/2003 | Foreman et al. |
| 2003/0105493 | A1 | 6/2003 | Salo |
| 2003/0114905 | A1 | 6/2003 | Kuzma |
| 2003/0149450 | A1 | 8/2003 | Mayberg |
| 2003/0158584 | A1 | 8/2003 | Cates et al. |
| 2003/0195578 | A1 | 10/2003 | Perron et al. |
| 2003/0212440 | A1 | 11/2003 | Boveja |
| 2003/0216792 | A1 | 11/2003 | Levin et al. |
| 2004/0049120 | A1 | 3/2004 | Cao et al. |
| 2004/0068299 | A1 | 4/2004 | Laske et al. |
| 2004/0077995 | A1 | 4/2004 | Ferek-Petric et al. |
| 2004/0122496 | A1 | 6/2004 | Zhang et al. |
| 2004/0122497 | A1 | 6/2004 | Zhang et al. |
| 2004/0122498 | A1 | 6/2004 | Zhang et al. |
| 2004/0186517 | A1 * | 9/2004 | Hill et al. ................. 607/2 |
| 2004/0199210 | A1 | 10/2004 | Shelchuk |
| 2004/0210261 | A1 * | 10/2004 | King et al. .............. 607/9 |
| 2004/0215286 | A1 | 10/2004 | Stypulkowski |
| 2004/0230241 | A1 | 11/2004 | Carlson et al. |
| 2004/0260374 | A1 | 12/2004 | Zhang et al. |
| 2004/0260375 | A1 | 12/2004 | Zhang et al. |
| 2005/0065553 | A1 | 3/2005 | Ben Ezra et al. |
| 2005/0065554 | A1 | 3/2005 | KenKnight et al. |
| 2005/0085864 | A1 | 4/2005 | Schulman et al. |
| 2005/0090719 | A1 | 4/2005 | Scheiner et al. |
| 2005/0096705 | A1 * | 5/2005 | Pastore et al. .............. 607/17 |
| 2005/0143779 | A1 | 6/2005 | Libbus |
| 2005/0143785 | A1 | 6/2005 | Libbus |
| 2005/0149126 | A1 | 7/2005 | Libbus |
| 2005/0149127 | A1 | 7/2005 | Libbus |
| 2005/0149128 | A1 | 7/2005 | Heil, Jr. et al. |
| 2005/0149129 | A1 | 7/2005 | Libbus et al. |
| 2005/0149130 | A1 | 7/2005 | Libbus |
| 2005/0149131 | A1 | 7/2005 | Libbus et al. |
| 2005/0149132 | A1 | 7/2005 | Libbus |
| 2005/0149133 | A1 | 7/2005 | Libbus et al. |
| 2005/0149143 | A1 | 7/2005 | Libbus et al. |
| 2005/0149155 | A1 | 7/2005 | Scheiner et al. |
| 2005/0149156 | A1 | 7/2005 | Libbus et al. |
| 2005/0154426 | A1 | 7/2005 | Boveja et al. |
| 2006/0079945 | A1 | 4/2006 | Libbus |
| 2006/0089592 | A1 | 4/2006 | Kadhiresan et al. |
| 2006/0095080 | A1 | 5/2006 | Libbus et al. |
| 2006/0106428 | A1 | 5/2006 | Libbus et al. |
| 2006/0106429 | A1 | 5/2006 | Libbus et al. |
| 2006/0116737 | A1 | 6/2006 | Libbus |
| 2006/0122675 | A1 | 6/2006 | Libbus et al. |
| 2006/0149337 | A1 * | 7/2006 | John ........................ 607/45 |
| 2006/0173493 | A1 * | 8/2006 | Armstrong et al. ............... 607/2 |
| 2006/0190044 | A1 | 8/2006 | Libbus et al. |
| 2006/0206153 | A1 | 9/2006 | Libbus et al. |
| 2006/0206154 | A1 * | 9/2006 | Moffitt et al. .................. 607/9 |
| 2006/0206158 | A1 | 9/2006 | Wu et al. |
| 2006/0206159 | A1 * | 9/2006 | Moffitt et al. ................... 607/37 |
| 2006/0217772 | A1 | 9/2006 | Libbus et al. |
| 2006/0224188 | A1 | 10/2006 | Libbus et al. |
| 2006/0224202 | A1 | 10/2006 | Moffitt et al. |
| 2006/0241697 | A1 | 10/2006 | Libbus et al. |
| 2006/0241699 | A1 | 10/2006 | Libbus et al. |
| 2006/0241725 | A1 | 10/2006 | Libbus et al. |
| 2006/0253161 | A1 | 11/2006 | Libbus et al. |
| 2006/0259083 | A1 | 11/2006 | Libbus et al. |
| 2006/0259085 | A1 | 11/2006 | Zhang et al. |
| 2006/0259107 | A1 | 11/2006 | Caparso et al. |
| 2006/0271108 | A1 | 11/2006 | Libbus et al. |
| 2006/0271118 | A1 | 11/2006 | Libbus et al. |
| 2006/0282131 | A1 | 12/2006 | Caparso et al. |
| 2006/0282145 | A1 | 12/2006 | Caparso et al. |
| 2007/0156207 | A1 * | 7/2007 | Kothandaraman et al. ...... 607/66 |
| 2008/0058872 | A1 | 3/2008 | Brockway et al. |
| 2010/0114226 | A1 | 5/2010 | Libbus et al. |
| 2012/0245656 | A1 | 9/2012 | Brockway et al. |

FOREIGN PATENT DOCUMENTS

| | | |
|---|---|---|
| EP | 1486232 A2 | 12/2004 |
| EP | 1541193 A1 | 6/2005 |
| WO | WO-01/24876 A1 | 4/2001 |
| WO | WO-01/76689 A2 | 10/2001 |
| WO | WO-03/018108 A2 | 3/2003 |
| WO | WO-03/076008 A1 | 9/2003 |
| WO | WO-03/082080 A2 | 10/2003 |
| WO | WO-2005/042091 A1 | 5/2005 |
| WO | WO-2005/063332 A1 | 7/2005 |
| WO | WO-2005/065771 A1 | 7/2005 |
| WO | WO-2005063332 A1 | 7/2005 |
| WO | WO-2006/101917 A2 | 9/2006 |
| WO | WO-2008/027233 A1 | 3/2008 |
| WO | WO-2008/027242 A2 | 3/2008 |

OTHER PUBLICATIONS

"U.S. Appl. No. 11/087,935, Response filed May 21, 2008 to Non-Final Office Action mailed Jan. 22, 2008", 14 pgs.

"U.S. Appl. No. 11/087,935, Non-Final Office Action mailed Jan. 22, 2008", 5 pgs.

"U.S. Appl. No. 11/087,935, Notice of Allowance mailed Mar. 27, 2009", 7 pgs.

"International Application Serial No. PCT/US2007/018371, Written Opinion mailed Dec. 28, 2007", 9 pgs.

"International Application Serial No. PCT/US2007/018371, International Search Report mailed Dec. 28, 2007", 6 pgs.

"International Application Serial No. PCT/US2007/018411, Invitation to Pay Fees and Partial International Search Report mailed Nov. 7, 2008", 4 pgs.

"International Application Serial No. PCT/US2007/018411, Search Report mailed Mar. 24, 2009", 6 pgs.

"International Application Serial No. PCT/US2007/018411, Written Opinion mailed Mar. 24, 2009", 10 pgs.

"International Application Serial No. PCT/US2006/008314, International Search Report and Written Opinion mailed Jul. 6, 2006", 13 pgs.

"International Application Serial No. PCT/US2004/043255, International Search Report mailed Apr. 29, 2005", 4 pgs.

Abraham, W. T., "Miracle Study Group. Multicenter InSync Randomized Clinical Evaluation. Cardiac resynchronization in chronic heart failure", *New England Journal of Medicine*, 346(24), (Jul. 13, 2002), 1845-1853.

Andersen, H., "Long-term follow-up of patients from a randomised trial of atrial versus ventricular pacing for sick-sinus syndrome", *Lancet*, 350(9086), (Oct. 25, 1997), 1210-6.

Benchimol, A., "Cardiac hemodynamics during stimulation of the right atrium, right ventricle, and left ventricle in normal and abnormal hearts", *Circulation*, 33(6), (Jun. 1966), 933-944.

Bevan, J. A., et al., "Postganglionic sympathetic delay in vascular smooth muscle", *Journal of Pharmacology & Experimental Therapeutics*, 152(2), (May 1966), 221-30.

Bevan, J. A., et al., "Sympathetic nerve-free vascular muscle", *Journal of Pharmacology & Experimental Therapeutics*, 157(1), (Jul. 1967), 117-24.

Bilgutay, A. M., "A new concept in the treatment of hypertension utilizing an implantable electronic device: "Baropacer"", *Trans Am Soc Artif Intern Organs.*, 10, (1964), 387-395.

Bilgutay, A. M., "Vagal tuning for the control of supraventricular arrhythmias", *Surgical Forum*, 16, (1965), 151-3.

Bilgutay, A. M., "Vagal tuning. A new concept in the treatment of supraventricular arrhythmias, angina pectoris, and heart failure", *Journal of Thoracic and Cardiovascular Surgery*, 56(1), (Jul. 1968), 71-82.

Borst, C., "Optimal frequency of carotid sinus nerve stimulation in treatment of angina pectoris", *Cardiovascular Research*, 8(5), (Sep. 1974), 674-80.

Braunwald, E., "Carotid sinus nerve stimulation in the treatment of angina pectoris and supraventricular tachycardia", *California Medicine*, 112(3), (Mar. 1970), 41-50.

Braunwald, E., "Relief of angina pectoris by electrical stimulation of the carotid-sinus nerves", *New England Journal of Medicine*, 277(24), (Dec. 14, 1967), 1278-83.

Chapleau, M. W., "Contrasting effects of static and pulsatile pressure on carotid baroreceptor activity in dogs", *Circulation*, vol. 61, No. 5, (Nov. 1987), 648-658.

Chapleau, M. W., "Pulsatile activation of baroreceptors causes central facilitation of baroreflex", *American Journal Physiol Heart Circ Physiol*, (Jun. 1989), 256: H1735-H1741.

Coleridge, J. C., et al., "Relationship between pulmonary arterial pressure and impulse activity in pulmonary arterial baroreceptor fibres", *Journal of Physiology*, 158, (Sep. 1961), 197-205.

Coleridge, J. C., "The distribution, connexions and histology of baroreceptors in the pulmonary artery, with some observations on the sensory innervation of the ductus arteriosus", *Journal of Physiology*, 156, (May 1961), 591-602.

Cooper, T. B., et al., "Neural effects on sinus rate and atrioventricular conduction produced by electrical stimulation from a transvenous electrode catheter in the canine right pulmonary artery", *Circulation Research*, vol. 46, No. 1, (Jan. 1980), 48-57.

Courtice, G. P., "Effect of frequency and impulse pattern on the non-cholinergic cardiac response to vagal stimulation in the toad, *Bufo marinus*", *Journal of the Autonomic Nervous System*, 48(3), (Aug. 1994), 267-272.

Dart Jr., C. H., "Carotid sinus nerve stimulation treatment of angina refractory to other surgical procedures", *Annals of Thoracic Surgery*, 11(4), (Apr. 1971), 348-59.

De Landsheere, D., "Effect of spinal cord stimulation on regional myocardial perfusion assessed by positron emission tomography", *American Journal of Cardiology*, 69(14), (May 1, 1992), 1143-1149.

Dunning, A. J, "Electrostimulation of the Carotid Sinus Nerve in Angina Pectoris", *University Department of Medicine*, Binnengasthuis, Amsterdam; Printed by Royal VanGorcum, Assen, Netherlands, (1971), 1-92.

Epstein, S. E., "Treatment of angina pectoris by electrical stimulation of the carotid-sinus nerves", *New England Journal of Medicine*, 280(18), (May 1, 1969), 971-978.

Farrehi, C., "Stimulation of the carotid sinus nerve in treatment of angina pectoris", *American Heart Journal*, 80(6), (Dec. 1970), 759-765.

Feliciano, L., "Vagal nerve stimulation releases vasoactive intestinal peptide which significantly increases coronary artery blood flow", *Cardiovascular Research*, 40(1), (Oct. 1998), 45-55.

Francis, G. S., et al., "Acute vasoconstrictor response to intravenous furosemide in patients with chronic congestive heart failure. Activation of the of neurohumoral axis", *Annals of Internal Medicine*, 103(1), (Jul. 1985), 1-6.

Fromer, M, "Ultrarapid subthreshold stimulation for termination of atrioventricular node reentrant tachycardia", *Journal of the American College of Cardiology*, 20(4), (Oct. 1992), 879-83.

Grassi, G., et al., "Baroreflex and non-baroreflex modulation of vagal cardiac control after myocardial infarction", *Am J Cardiol.*, 84(5), (Sep. 1, 1999), 525-9.

Griffith, L. S. C., et al., "Electrical Stimulation of the Carotid Sinus Nerve in Normotensive and Renal Hypertensive Dogs", *Circulation*, 28, (Jul.-Dec. 1963), p. 730.

Henning, R. J., "Effects of autonomic nerve stimulation, asynchrony, and load on $dP/dt_{max}$ and on $dP/dt_{min}$", *American Journal of Physiology*, 260(4 Pt 2), (Apr. 1991), H1290-H1298.

Henning, R. J., "Vagal nerve stimulation increases right ventricular contraction and relaxation and heart rate", *Cardiovascular Research*, 32(5), (Nov. 1996), 846-853.

Henning, R. J., "Vagal stimulation attenuates sympathetic enhancement of left ventricular function", *American Journal of Physiology*, 258(5 Pt 2), (May 1990), H1470-H1475.

Hood Jr., W. B., et al., "Asynchronous contraction due to late systolic bulging at left ventricular pacing sites", *American Journal of Physiology*, 217(1), (Jul. 1969), 215-221.

Ishise, H., "Time course of sympathovagal imbalance and left ventricular dysfunction in conscious dogs with heart failure", *Journal of Applied Physiology*, 84(4), (Apr. 1998), 1234-1241.

Jessurun, G A, "Coronary blood flow dynamics during transcutaneous electrical nerve stimulation for stable angina pectoris associated with severe narrowing of one major coronary artery", *American Journal of Cardiology*, 82(8), erratum appears in Am J Cardiol. Feb. 15, 1999;83(4):642, (Oct. 15, 1998), 921-926.

Kandel, E. R., et al., "Part VII: Arousal, Emotion, and Behavioral Homeostasis", In: *Principles of neural science*, New York : McGraw-Hill, Health Professions Division, (2000), 966-969.

Karpawich, P. P., et al., "Altered cardiac histology following apical right ventricular pacing in patients with congenital atrioventricular block", *Pacing Clin Electrophysiol.*, 22(9), (Sep. 1999), 1372-1377.

Leclercq, C., et al., "Hemodynamic importance of preserving the normal sequence of ventricular activation in permanent cardiac pacing", *Am Heart J.*, 129(6), (Jun. 1995), 1133-1141.

Li, M., "Vagal nerve stimulation markedly improves long-term survival after chronic heart failure in rats", *Circulation*, 109(1), (2004), 120-124.

Mannheimer, C., "Epidural spinal electrical stimulation in severe angina pectoris", *British Heart Journal*, 59(1), (Jan. 1988), 56-61.

Mannheimer, C., "Transcutaneous electrical nerve stimulation (TENS) in angina pectoris", *Pain*, 26(3), (Sep. 1986), 291-300.

Mannheimer, C., "Transcutaneous electrical nerve stimulation in severe angina pectoris", *European Heart Journal*, 3(4), (Aug. 1982), 297-302.

Mazgalev, T. N., "Autonomic modification of the atrioventricular node during atrial fibrillation: role in the slowing of ventricular rate", *Circulation*, 99(21), (Jun. 1, 1999), 2806-2814.

Millar-Craig, M W, et al., "Circadian variation of blood-pressure", *Lancet*, 1(8068), (Apr. 15, 1978), 795-797.

Minisi, A. J., et al., "Regional left ventricular deafferentation increases baroreflex sensitivity following myocardial infarction", *Cardiovasc Res.*, 58(1), (Apr. 1, 2003), 136-141.

Murphy, D. F., "Intractable angina pectoris: management with dorsal column stimulation", *Medical Journal of Australia*, 146(5), (Mar. 2, 1987), p. 260.

Neistadt, A., "Effects of electrical stimulation of the carotid sinus nerve in reversal of experimentally induced hypertension", *Surgery*, 61(6), (Jun. 1967), 923-931.

Nolan, J., et al., "Prospective Study of Heart Rate Variability and Mortality in Chronic Heart Failure: Results of the United Kingdom Heart Failure Evaluation and Assessment of Risk Trial (UK-Heart).", *Circulation*, 98(15), (1998), 1510-1516.

Peters, T. K., "Temporal and spatial summation caused by aortic nerve stimulation in rabbits. Effects of stimulation frequencies and amplitudes", *Journal of the Autonomic Nervous System*, 27(3), (Aug. 1989), 193-205.

Peters, T. K., "The principle of electrical carotid sinus nerve stimulation: a nerve pacemaker system for angina pectoris and hypertension therapy", *Annals of Biomedical Engineering*, 8(4-6), (1980), 445-458.

Philbin, D. M., "Inappropriate shocks delivered by an ICD as a result of sensed potentials from a transcutaneous electronic nerve stimulation unit", *Pacing & Clinical Electrophysiology*, 21(10), (Oct. 1998), 2010-2011.

Prakash, P., "Asymmetrical distribution of aortic nerve fibers in the pig", *Anat Rec.*, 158(1), (May 1967), 51-7.

Rosenqvist, M., "The effect of ventricular activation sequence on cardiac performance during pacing", *Pacing and Electrophysiology*, 19(9), (1996), 1279-1286.

Rushmer, R. F, "Chapter 5—Systemic Arterial Pressure", In: *Cardiovascular dynamics*, Philadelphia : Saunders, (1976), 176-216.

Schauerte, P., "Catheter stimulation of cardiac parasympathetic nerves in humans: a novel approach to the cardiac autonomic nervous system", *Circulation*, 104(20), (Nov. 13, 2001), 2430-5.

Schauerte, P., "Ventricular rate control during atrial fibrillation by cardiac parasympathetic nerve stimulation: a transvenous approach", *Journal of the American College of Cardiology*, 34(7), (Dec. 1999), 2043-50.

Schauerte, P. N., et al., "Transvenous parasympathetic cardiac nerve stimulation: an approach for stable sinus rate control", *Journal of Cardiovascular Electrophysiology*, 10(11), (Nov. 1999), 1517-24.

Schauerte, P. N, "Transvenous Parasympathetic Nerve Stimulation in the Inferior Vena Cava and Atrioventricular Conduction", *Journal of Cardiovascular Electrophysiology*, 11(1), (Jan. 2000), 64-69.

Scherlag, M. A., "Endovascular Neural Stimulation Via a Novel Basket Electrode Catheter: Comparison of Electrode Configurations", *Journal of Interventional Cardiac Electrophysiology*, 4(1), (Apr. 2000), 219-224.

Sigurdsson, A., et al., "The Role of Neurohormonal Activation in Chronic Heart Failure and Postmyocardial Infarction", *American Heart Journal*, 132 (1 Pt 2 Su), (Jul. 1996), 229-234.

Takahashi, N., "Vagal modulation of ventricular tachyarrhythmias induced by left ansae subclaviae stimulation in rabbits", *Japanese Heart Journal*, 39(4), (Jul. 1998), 503-11.

Tse, H. F., et al., "Long-term effect of right ventricular pacing on myocardial perfusion and function", *J Am Coll Cardiol.*, 29(4), (Mar. 15, 1997), 744-749.

Vanoli, E., "Vagal stimulation and prevention of sudden death in conscious dogs with a healed myocardial infarction", *Circulation Research*, 68(5), (May 1991), 1471-1481.

Veerman, D. P., et al., "Circadian profile of systemic hemodynamics", *Hypertension*, 26(1), (Jul. 1995), 55-59.

Verity, M. A., et al., "Plurivesicular nerve endings in the pulmonary artery", *Nature*, 211(48), (Jul. 30, 1966), 537-538.

Verity, M., et al., "Pulmonary artery innervation: a morphopharmacologic correlation", *Proceedings of the Western Pharmacology Society*, 8, (1965), 57-59.

Wallick, D. W., "Selective AV nodal vagal stimulation improves hemodynamics during acute atrial fibrillation in dogs", *American Journal of Physiology—Heart & Circulatory Physiology*, 281(4), (Oct. 2001), H1490-H1497.

Waninger, M. S., "Electrophysiological control of ventricular rate during atrial fibrillation", *Pacing & Clinical Electrophysiology*, 23(8), (Aug. 2000), 1239-1244.

Wiggers, C. J., et al., "The muscular reactions of the mammalian ventricles to artificial surface stimuli", *American Journal of Physiology*, (1925), 346-378.

Zhang, Y., "Optimal ventricular rate slowing during atrial fibrillation by feedback AV nodal-selective vagal stimulation", *American Journal of Physiology—Heart & Circulatory Physiology*, 282(3), (Mar. 2002), H1102-H1110.

Zhou, X., "Prevention of high incidence of neurally mediated ventricular arrhythmias by afferent nerve stimulation in dogs", *Circulation*, 101(7), (Feb. 22, 2000), 819-24.

"European Application Serial No. 07837051.7, Communication mailed Feb. 25, 2010", 3 pgs.

"European Application Serial No. 07837051.7, Communication mailed Apr. 23, 2009", 1 pg.

"European Application Serial No. 07837051.7, Response filed May 27, 2009 to Communication mailed Apr. 23, 2009", 8 pgs.

"U.S. Appl. No. 11/468,143, Non-Final Office Action mailed Oct. 6, 2009", 8 pgs.

"U.S. Appl. No. 11/468,143, Notice of Allowance mailed May 18, 2010", 7 pgs.

"U.S. Appl. No. 11/468,143, Response filed Jul. 16, 2009 to Restriction Requirement mailed Jun. 16, 2009", 9 pgs.

"U.S. Appl. No. 11/468,143, Response filed Feb. 8, 2010 to Non Final Office Action mailed Oct. 6, 2009", 9 pgs.

"U.S. Appl. No. 11/468,143, Restriction Requirement mailed Jun. 16, 2009", 10 pgs.

"Australian Application Serial No. 2007290727, First Examiner Report mailed Sep. 15, 2010", 3 pgs.

"European Application Serial No. 07837051.7, Response filed Jun. 24, 2010 Office Action dated Feb. 25, 2010", 10 pgs.

"U.S. Appl. No. 12/686,704, Final Office Action mailed Nov. 9, 2012", 7 pgs.

"U.S. Appl. No. 12/686,704, Response filed Sep. 20, 2012 to Non Final Office Action mailed Jun. 29, 2012", 17 pgs.

"Chinese Application Serial No. 200780032255.4, Response filed Sep. 10, 2012 to Office Action mailed Jun. 26, 2012", (w/ English Translation of Claims), 6 pgs.

"International Application Serial No. PCT/US2007/018371. International Preliminary Report on Patentability mailed Mar. 12, 2009", 10 pgs.

* cited by examiner

SYSTEM AND METHOD FOR NEURAL STIMULATION

RELATED APPLICATIONS

This application is related to U.S. patent application Ser. No. 11/087,935 filed Mar. 23, 2005, now U.S. Pat. No. 7,660, 628 to U.S. patent application Ser. No. 11/468,143 filed Aug. 29, 2006, now U.S. Pat. No. 7,801,604, the disclosures of which are hereby incorporated by reference in their entirety.

TECHNICAL FIELD

This application relates generally to medical devices and, more particularly, to systems, devices and methods to provide myocardial and neural stimulation.

BACKGROUND

Implanting a chronic electrical stimulator, such as a cardiac stimulator, to deliver medical therapy(ies) is known. Examples of cardiac stimulators include implantable cardiac rhythm management (CRM) devices such as pacemakers, implantable cardiac defibrillators (ICDs), and implantable devices capable of performing pacing and defibrillating functions. Implantable CRM devices provide electrical stimulation to selected portions of the heart in order to treat disorders of cardiac rhythm, generally referred to herein as CRM functions/therapy. An implantable pacemaker, for example, is a CRM device that paces the heart with timed pacing pulses. The pacing pulses can be timed from other pacing pulses or sensed electrical activity. If functioning properly, the pacemaker makes up for the heart's inability to pace itself at an appropriate rhythm in order to meet metabolic demand by enforcing a minimum heart rate. Some CRM devices synchronize pacing pulses delivered to different areas of the heart in order to coordinate the contractions. Coordinated contractions allow the heart to pump efficiently while providing sufficient cardiac output. Clinical data has shown that cardiac resynchronization, achieved through synchronized biventricular pacing, results in a significant improvement in cardiac function. Cardiac resynchronization therapy improves cardiac function in heart failure patients.

Heart failure patients have abnormal autonomic balance, which is associated with LV dysfunction and increased mortality. Modulation of the sympathetic and parasympathetic nervous systems has potential clinical benefit in preventing remodeling and death in heart failure and post-MI patients. Direct electrical stimulation can activate the baroreflex, inducing a reduction of sympathetic nerve activity and reducing blood pressure by decreasing vascular resistance. Sympathetic inhibition and parasympathetic activation have been associated with reduced arrhythmia vulnerability following a myocardial infarction, presumably by increasing collateral perfusion of the acutely ischemic myocardium and decreasing myocardial damage.

SUMMARY

Various aspects of the present subject matter provide an implantable device. In various embodiments, the device comprises at least one port, where each port is adapted to connect a lead with an electrode to the device. The device further includes a stimulation platform, including a sensing circuit connected to the at least one port to sense an intrinsic cardiac signal and a stimulation circuit connected to the at least one port via a stimulation channel to deliver a stimulation signal through the stimulation channel to the electrode. The stimulation circuit is adapted to deliver stimulation signals through the stimulation channel for both neural stimulation therapy and CRM therapy. The sensing and stimulation circuits are adapted to perform CRM functions. The device further includes a controller connected to the sensing circuit and the stimulation circuit to control the neural stimulation therapy and the CRM therapy.

Various aspects of the present subject matter provide a method for operating an implantable device to deliver a desired stimulation signal through a stimulation channel to an electrode. In an embodiment of the method, a desired therapy to be delivered through the stimulation channel to the electrode is determined. Upon determining that a cardiac rhythm management (CRM) therapy is desired, a CRM stimulation signal is delivered through the stimulation channel to the electrode to capture a heart muscle. Upon determining that a neural stimulation therapy is desired, a neural stimulation signal is delivered through the stimulation channel to the electrode to elicit a neural response.

Various aspects of the present subject matter provide a method for making an implantable medical device. In an embodiment of the method, a controller is connected to a memory, to a sensing module adapted to sense intrinsic cardiac signals over a sensing channel from an electrode, and to a stimulation module adapted to generate stimulation signals on a stimulation channel to the electrode. Computer instructions to be performed by the controller are stored in the memory. The computer instructions include instructions to perform a neural stimulation therapy using the stimulation module and to perform a cardiac rhythm management (CRM) therapy using the sensing module and the stimulation module. The computer instructions further include instructions to receive a therapy selection input, to generate a neural stimulation signal on the stimulation channel to the electrode if the neural stimulation therapy is selected, and to generate a CRM stimulation signal on the stimulation channel to the electrode if the neural CRM therapy is selected.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their equivalents.

DETAILED DESCRIPTION

Figure 1B:
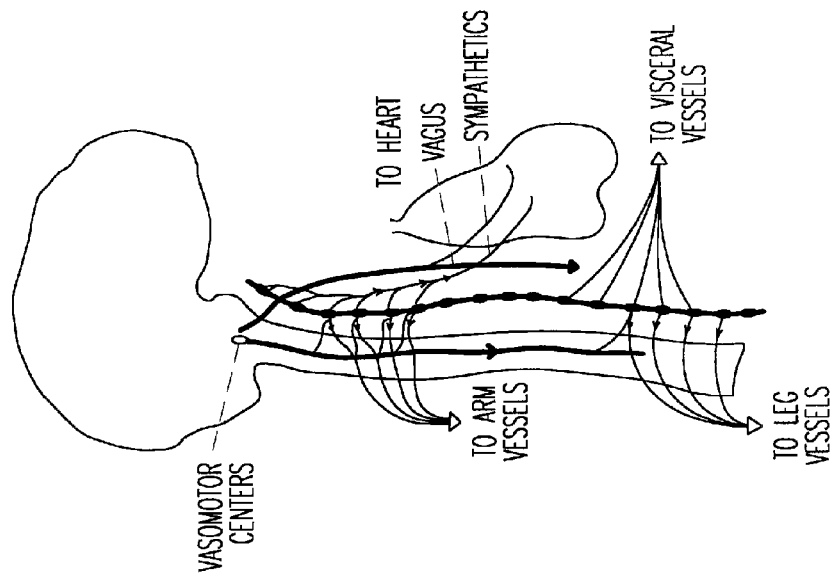
FIGS. 1A and 1B illustrate neural mechanisms for peripheral vascular control.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Disclosed herein is a device in which a common hardware platform is used to provide both neural stimulation and CRM stimulation, also referred to herein as myocardial stimulation, thus reducing the hardware requirements to perform both CRM and NS therapies. The reduced hardware requirements can reduce the cost and size of the device. Various device embodiments include hardware capable of alternating between myocardial stimulation and neural stimulation, and various device embodiments include hardware to provide a common stimulation waveform capable of simultaneously activating the myocardium and the nerve. For example, one embodiment switches between stimulation modes, in which the device delivers a stimulating waveform suitable for cardiac pacing, neural stimulation, or both cardiac pacing and neural stimulation is delivered. These different stimulation waveforms can be delivered at different sites (through the CRM lead(s) or through the neural stimulation lead(s)). In some embodiments, neural stimulation waveforms are delivered through dedicated leads and cardiac pacing waveforms are delivered through dedicated leads; and in some embodiments, the neural stimulation and cardiac pacing waveforms are delivered at alternating times through the same lead(s).

Some CRM devices have the ability in hardware to provide electrical stimulation at the appropriate amplitude and frequency for neural stimulation such as burst pacing at frequencies up to 50 Hz. Examples of neural stimulation leads include an expandable stimulation lead placed in the pulmonary artery in the proximity of a high concentration of baroreceptors, an intravascularly-inserted lead placed proximal to and adapted to transvascularly stimulate a cardiac fat pad, an epicardial lead placed in a cardiac fat pad, a cuff electrode placed around a nerve trunk such as the aortic, carotid or vagus nerve, and an intravascularly-inserted lead placed proximal to and adapted to transvascularly stimulate a nerve trunk such as the aortic, carotid or vagus nerve.

In various embodiments, the implantable device uses a lead positioned to provide either myocardial stimulation, to provide neural stimulation, or to simultaneously provide both myocardial stimulation and neural stimulation by delivering a waveform through the appropriately placed stimulation lead that stimulates the myocardium and the nerve. Thus, through a judicious selection of stimulation waveforms, this embodiment does not switch between modes, but accomplishes simultaneous cardiac and neural stimulation. Other waveforms are applied if it is desired to provide only cardiac pacing or neural stimulation, but not both.

The stimulation device of the present subject matter uses a common or shared hardware platform to provide both CRM therapy (pacing, CRT, etc.) and neural stimulation through either a common or an independent lead. Some device embodiments switch between output modes, using the same hardware to provide cardiac pacing and neural stimulation. Typically, cardiac pacing occurs at a relatively lower frequency and larger amplitude than neural stimulation.

CRM therapy (such as brady pacing and/or CRT) is capable of being provided in conjunction with neural stimulation (such as anti-remodeling therapy) without requiring additional hardware than that which already exists in CRM hardware. Various embodiments use existing CRM output channel(s) adapted to exclusively provide neural stimulation, use existing CRM output channel(s) adapted to alternate between cardiac and neural stimulation, and use existing CRM output channel(s) adapted to simultaneously provide cardiac and neural stimulation.

The stimulation platform for an existing CRM device retains the existing pulse generator, pacing algorithms, and output circuitry. In an embodiment, the device intermittently suspends cardiac pacing and delivers neural stimulation using a shared platform. In other embodiments, an existing CRM lead is placed in a location so as to provide either cardiac or neural stimulation, or both, depending on the stimulating waveform.

The following disclosure provides a discussion of physiology and examples of therapies capable of being performed by the present subject matter, and further provides a discussion of an implantable medical device and methods according to the present subject matter.

Physiology

Heart Failure

Heart failure refers to a clinical syndrome in which cardiac function causes a below normal cardiac output that can fall below a level adequate to meet the metabolic demand of peripheral tissues. Heart failure may present itself as congestive heart failure (CHF) due to the accompanying venous and pulmonary congestion. Heart failure can be due to a variety of etiologies such as ischemic heart disease.

Hypertension

Hypertension is a cause of heart disease and other related cardiac co-morbidities. Hypertension occurs when blood vessels constrict. As a result, the heart works harder to maintain flow at a higher blood pressure, which can contribute to heart failure. Hypertension generally relates to high blood pressure, such as a transitory or sustained elevation of systemic arterial blood pressure to a level that is likely to induce cardiovascular damage or other adverse consequences. Hypertension has been arbitrarily defined as a systolic blood pressure above 140 mm Hg or a diastolic blood pressure above 90 mm Hg. Consequences of uncontrolled hypertension include, but are not limited to, retinal vascular disease and stroke, left ventricular hypertrophy and failure, myocardial infarction, dissecting aneurysm, and renovascular disease.

A large segment of the general population, as well as a large segment of patients implanted with pacemakers or defibrillators, suffer from hypertension. The long term mortality as well as the quality of life can be improved for this population if blood pressure and hypertension can be reduced. Many patients who suffer from hypertension do not respond to treatment, such as treatments related to lifestyle changes and hypertension drugs.

Cardiac Remodeling

Following myocardial infarction (MI) or other cause of decreased cardiac output, a complex remodeling process of the ventricles occurs that involves structural, biochemical, neurohormonal, and electrophysiologic factors. Ventricular remodeling is triggered by a physiological compensatory mechanism that acts to increase cardiac output due to so-called backward failure which increases the diastolic filling pressure of the ventricles and thereby increases the so-called preload (i.e., the degree to which the ventricles are stretched by the volume of blood in the ventricles at the end of diastole). An increase in preload causes an increase in stroke volume during systole, a phenomena known as the Frank-Starling principle. When the ventricles are stretched due to the increased preload over a period of time, however, the ventricles become dilated. The enlargement of the ventricular volume causes increased ventricular wall stress at a given systolic pressure. Along with the increased pressure-volume work done by the ventricle, this acts as a stimulus for hypertrophy of the ventricular myocardium. The disadvantage of dilatation is the extra workload imposed on normal, residual myocardium and the increase in wall tension (Laplace's Law) which represent the stimulus for hypertrophy. If hypertrophy is not adequate to match increased tension, a vicious cycle ensues which causes further and progressive dilatation.

As the heart begins to dilate, afferent baroreceptor and cardiopulmonary receptor signals are sent to the vasomotor central nervous system control center, which responds with hormonal secretion and sympathetic discharge. It is the combination of hemodynamic, sympathetic nervous system and hormonal alterations (such as presence or absence of angiotensin converting enzyme (ACE) activity) that ultimately account for the deleterious alterations in cell structure involved in ventricular remodeling. The sustained stresses causing hypertrophy induce apoptosis (i.e., programmed cell death) of cardiac muscle cells and eventual wall thinning which causes further deterioration in cardiac function. Thus, although ventricular dilation and hypertrophy may at first be compensatory and increase cardiac output, the processes ultimately result in both systolic and diastolic dysfunction. It has been shown that the extent of ventricular remodeling is positively correlated with increased mortality in post-MI and heart failure patients.

Nervous System

The automatic nervous system (ANS) regulates "involuntary" organs, while the contraction of voluntary (skeletal) muscles is controlled by somatic motor nerves. Examples of involuntary organs include respiratory and digestive organs, and also include blood vessels and the heart. Often, the ANS functions in an involuntary, reflexive manner to regulate glands, to regulate muscles in the skin, eye, stomach, intestines and bladder, and to regulate cardiac muscle and the muscle around blood vessels, for example.

The ANS includes the sympathetic nervous system and the parasympathetic nervous system. The sympathetic nervous system is affiliated with stress and the "fight or flight response" to emergencies. Among other effects, the "fight or flight response" increases blood pressure and heart rate to increase skeletal muscle blood flow, and decreases digestion to provide the energy for "fighting or fleeing." The parasympathetic nervous system is affiliated with relaxation and the "rest and digest response" which, among other effects, decreases blood pressure and heart rate, and increases digestion to conserve energy. The ANS maintains normal internal function and works with the somatic nervous system.

Figure 1A:
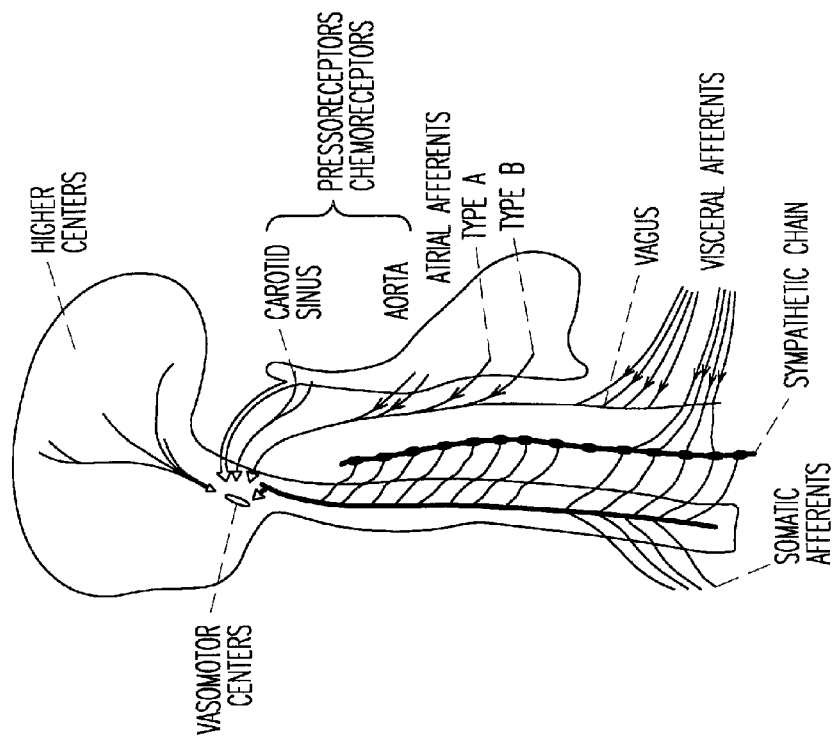

The heart rate and force is increased when the sympathetic nervous system is stimulated, and is decreased when the sympathetic nervous system is inhibited (the parasympathetic nervous system is stimulated). FIGS. 1A and 1B illustrate neural mechanisms for peripheral vascular control. FIG. 1A generally illustrates afferent nerves to vasomotor centers. An afferent nerve conveys impulses toward a nerve center. A vasomotor center relates to nerves that dilate and constrict blood vessels to control the size of the blood vessels. FIG. 1B generally illustrates efferent nerves from vasomotor centers. An efferent nerve conveys impulses away from a nerve center.

Stimulating the systematic and parasympathetic nervous systems can have effects other than heart rate and blood pressure. For example, stimulating the sympathetic nervous system dilates the pupil, reduces saliva and mucus production, relaxes the bronchial muscle, reduces the successive waves of involuntary contraction (peristalsis) of the stomach and the motility of the stomach, increases the conversion of glycogen to glucose by the liver, decreases urine secretion by the kidneys, and relaxes the wall and closes the sphincter of the bladder. Stimulating the parasympathetic nervous system (inhibiting the sympathetic nervous system) constricts the pupil, increases saliva and mucus production, contracts the bronchial muscle, increases secretions and motility in the stomach and large intestine, and increases digestion in the small intention, increases urine secretion, and contracts the wall and relaxes the sphincter of the bladder. The functions associated with the sympathetic and parasympathetic nervous systems are many and can be complexly integrated with each other.

Baroreflex is a reflex triggered by stimulation of a baroreceptor. A baroreceptor includes any sensor of pressure changes, such as sensory nerve endings in the wall of the auricles of the heart, vena cava, aortic arch and carotid sinus, that is sensitive to stretching of the wall resulting from increased pressure from within, and that functions as the receptor of the central reflex mechanism that tends to reduce that pressure. Clusters of nerve cells can be referred to as autonomic ganglia. These nerve cells can also be electrically stimulated to induce a baroreflex, which inhibits the sympathetic nerve activity and stimulates parasympathetic nerve activity. Autonomic ganglia thus forms part of a baroreflex pathway. Afferent nerve trunks, such as the vagus, aortic and carotid nerves, leading from the sensory nerve endings also form part of a baroreflex pathway. Stimulating a baroreflex pathway and/or baroreceptors inhibits sympathetic nerve activity (stimulates the parasympathetic nervous system) and reduces systemic arterial pressure by decreasing peripheral vascular resistance and cardiac contractility. Baroreceptors are naturally stimulated by internal pressure and the stretching of vessel wall (e.g. arterial wall).

Some aspects of the present subject matter locally stimulate specific nerve endings in arterial walls rather than stimulate afferent nerve trunks in an effort to stimulate a desired response (e.g. reduced hypertension) while reducing the undesired effects of indiscriminate stimulation of the nervous system. For example, some embodiments stimulate baroreceptor sites in the pulmonary artery. Some embodiments of the present subject matter involve stimulating baroreceptor sites or nerve endings in the aorta and the chambers of the heart, and some embodiments of the present subject matter involve stimulating an afferent nerve trunk, such as the vagus, carotid and aortic nerves. Some embodiments stimulate afferent nerve trunks using a cuff electrode, and some embodiments stimulate afferent nerve trunks using an intravascular lead positioned in a blood vessel proximate to the nerve, such that the electrical stimulation passes through the vessel wall to stimulate the afferent nerve trunk.

Figure 3:
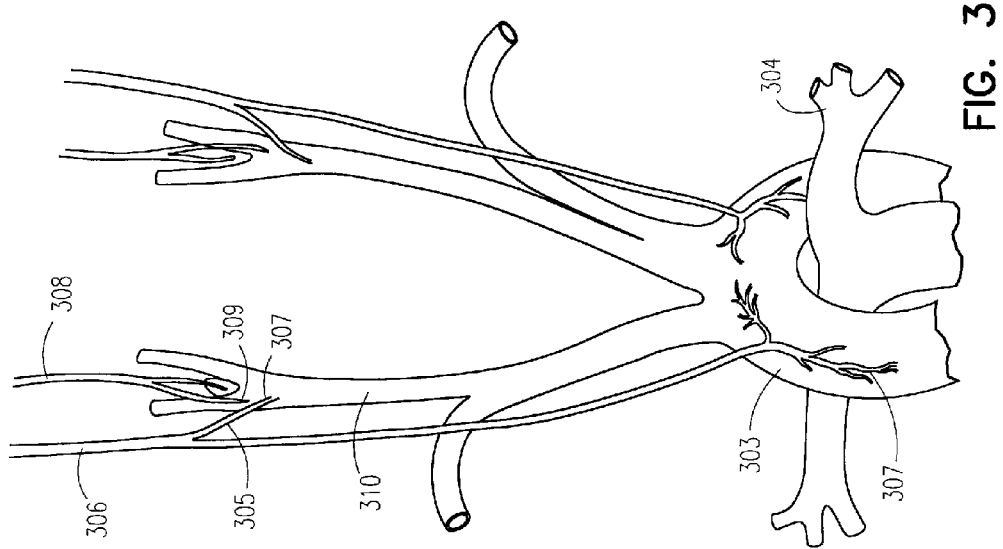
FIG. 3 illustrates baroreceptors in the area of the carotid sinus, aortic arch and pulmonary artery.
Figure 2:
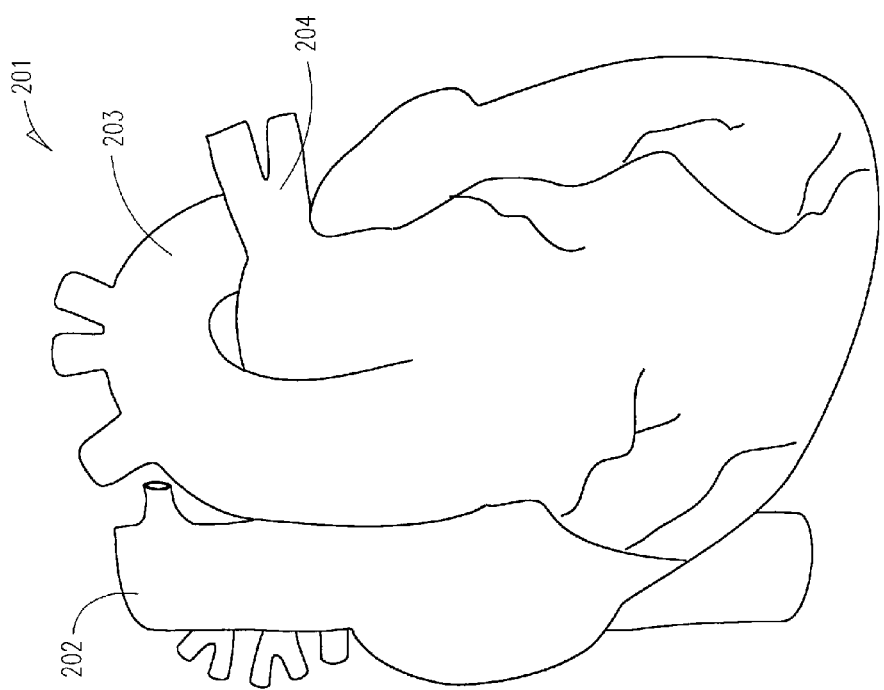
FIG. 2 illustrates a heart.
Figure 5:
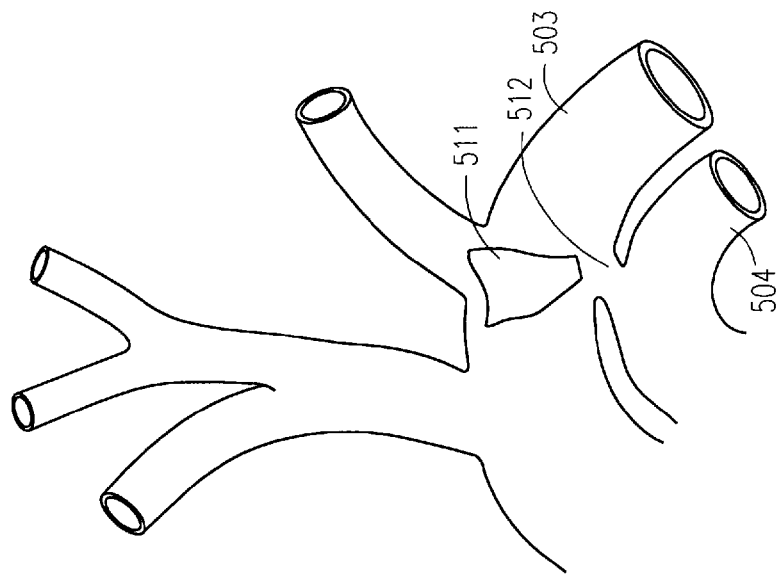
FIG. 5 illustrates baroreceptor fields in the aortic arch, near the ligamentum arteriosum and the trunk of the pulmonary artery.
Figure 4:
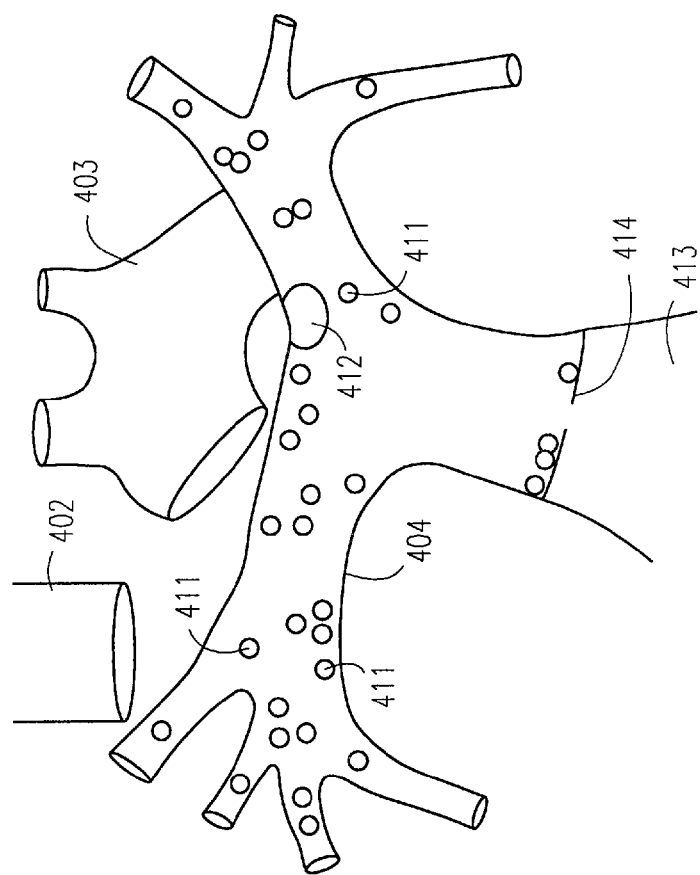
FIG. 4 illustrates baroreceptors in and around a pulmonary artery.

FIG. 2 illustrates a heart 201, a superior vena cava 202, an aortic arch 203, and a pulmonary artery 204 for providing a contextual relationship with the illustrations in FIGS. 3-5. As is discussed in more detail below, the pulmonary artery 204 includes baroreceptors. A lead is capable of being intravascularly inserted through a peripheral vein and through the tricuspid valve into the right ventricle of the heart (not expressly shown in the figure) similar to a cardiac pacemaker lead, and continue from the right ventricle through the pulmonary valve into the pulmonary artery. A portion of the pulmonary artery and aorta are proximate to each other. Various embodiments stimulate baroreceptors in the aorta using a lead intravascularly positioned in the pulmonary artery. Thus, according to various aspects of the present subject matter, the baroreflex is stimulated in or around the pulmonary artery by at least one electrode intravascularly inserted into the pulmonary artery. Alternatively, a wireless stimulating device, with or without pressure sensing capability, may be positioned via catheter into the pulmonary artery. Control of stimulation and/or energy for stimulation may be supplied by another implantable or external device via ultrasonic, electromagnetic or a combination thereof. Aspects of the present subject matter provide a relatively noninvasive surgical technique to implant a baroreflex stimulator intravascularly into the pulmonary artery.

FIG. 3 illustrates baroreceptors in the area of the carotid sinus 305, aortic arch 303 and pulmonary artery 304. The aortic arch 303 and pulmonary artery 304 were previously illustrated with respect to the heart in FIG. 2. As illustrated in FIG. 3, the vagus nerve 306 extends and provides sensory nerve endings 307 that function as baroreceptors in the aortic arch 303, in the carotid sinus 305 and in the common carotid artery 310. The glossopharyngeal nerve 308 provides nerve endings 309 that function as baroreceptors in the carotid sinus 305. These nerve endings 307 and 309, for example, are sensitive to stretching of the wall resulting from increased pressure from within. Activation of these nerve endings reduce pressure. Although not illustrated in the figures, the atrial and ventricular chambers of the heart also include baroreceptors. Cuffs have been placed around afferent nerve trunks, such as the vagal nerve, leading from baroreceptors to vasomotor centers to stimulate the baroreflex. According to various embodiments of the present subject matter, afferent nerve trunks can be stimulated using a cuff or intravascularly-fed lead positioned in a blood vessel proximate to the afferent nerves.

FIG. 4 illustrates baroreceptors in and around a pulmonary artery 404. The superior vena cava 402 and the aortic arch 403 are also illustrated. As illustrated, the pulmonary artery 404 includes a number of baroreceptors 411, as generally indicated by the dark area. Furthermore, a cluster of closely spaced baroreceptors is situated near the attachment of the ligamentum arteriosum 412. FIG. 4 also illustrates the right ventricle 413 of the heart, and the pulmonary valve 414 separating the right ventricle 413 from the pulmonary artery 404. According to various embodiments of the present subject matter, a lead is inserted through a peripheral vein and threaded through the tricuspid valve into the right ventricle, and from the right ventricle 413 through the pulmonary valve 414 and into the pulmonary artery 404 to stimulate baroreceptors in and/or around the pulmonary artery. In various embodiments, for example, the lead is positioned to stimulate the cluster of baroreceptors near the ligamentum arteriosum 412. FIG. 5 illustrates baroreceptor fields 511 in the aortic arch 503, near the ligamentum arteriosum 512 and the trunk of the pulmonary artery 504. Some embodiments position the lead in the pulmonary artery to stimulate baroreceptor sites in the aorta.

Figure 6:
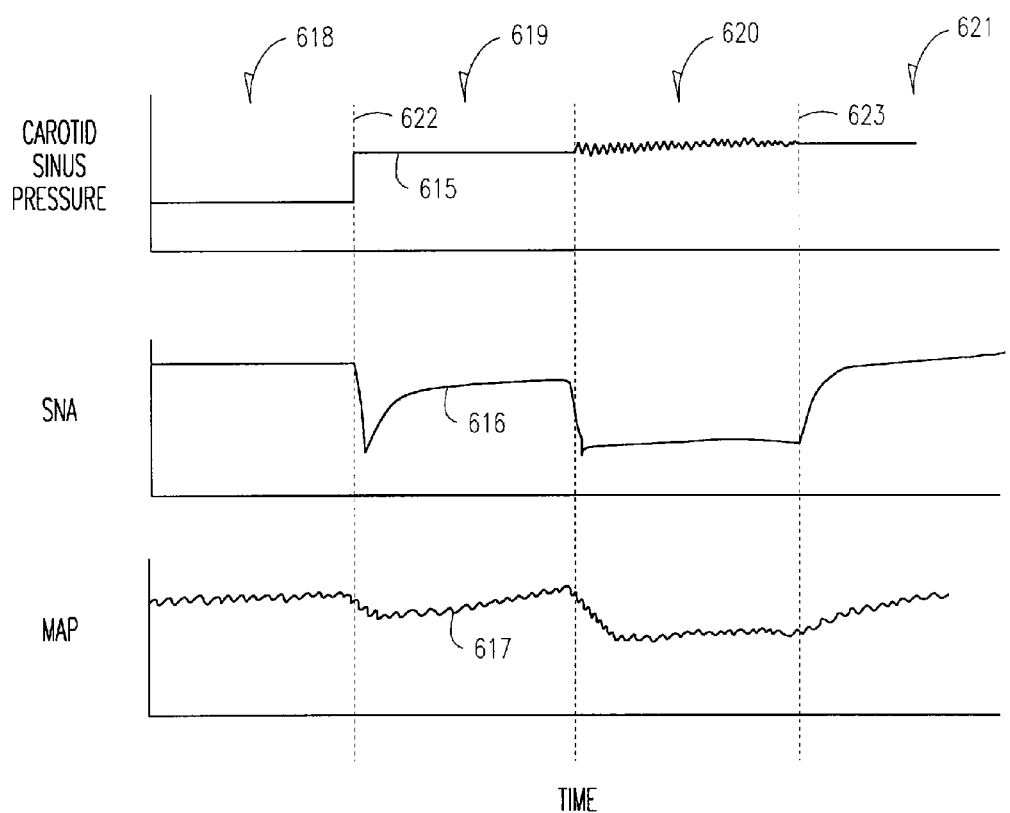
FIG. 6 illustrates baroreflex adaptation using a relationship between carotid sinus pressure, sympathetic nerve activity (SNA) and mean arterial pressure (MAP).

Nerves can adapt to stimulation, such that the effectiveness of continuous stimulation diminishes over time. Embodiments of the present subject matter provide neural stimulation that accounts for neural adaption. FIG. 6 illustrates baroreflex adaptation using a relationship between carotid sinus pressure 615, sympathetic nerve activity (SNA) 616 and mean arterial pressure (MAP) 617. Internal pressure and stretching of the arterial wall, such as that which occurs at the carotid sinus, naturally activates the baroreflex and the baroreflex inhibits SNA. The carotid sinus pressure, the SNA and the MAP are illustrated for the following four time segments: (1) relatively low and constant carotid sinus pressure 615 indicated at 618; (2) relatively high and constant carotid sinus pressure 615 indicated at 619; (3) relatively high and pulsed carotid sinus pressure 615 indicated at 620; and (4) a return to a relatively high and constant carotid sinus pressure 615 indicated at 621. When the carotid sinus pressure is relatively low and constant, as illustrated at 618, the SNA is relatively high and constant, and the pulsating MAP is relatively high. When the carotid sinus pressure is increased to a relatively high and constant pressure at transition 622, the SNA and MAP initially decrease due to the baroreflex and then increases due to the quick adaptation of the baroreflex to the increased carotid sinus pressure. However, when the carotid sinus pressure pulsates similar to naturally-occurring blood pressure pulses, as illustrated at 620, the SNA and MAP decrease to relatively low levels and are maintained at these relatively low levels. When the carotid sinus pressure changes from a pulsed to constant pressure at transition 623, the SNA and MAP both increase again due to the adaptation of the baroreflex. Various embodiments modulate the neural stimulation to mimic the effects of the naturally-occurring pulse pressure and prevent adaptation. For example, the amplitude, frequency, wave morphology, burst frequency and/or duration can be adjusted to abate adaptation.

Therapies

Neural stimulation may be delivered by an implantable device with or without delivery of other therapies. For example, a combination of neural stimulation and myocardial stimulation by a cardiac rhythm management (CRM) device may be used in a number of therapies, some of which are discussed below. For example, combining neural stimulation with CRM therapy provides benefits in treating hypertension, and combining neural stimulation with cardiac rhythm therapy (CRT) provides benefits in treating cardiac remodeling.

Figure 7:
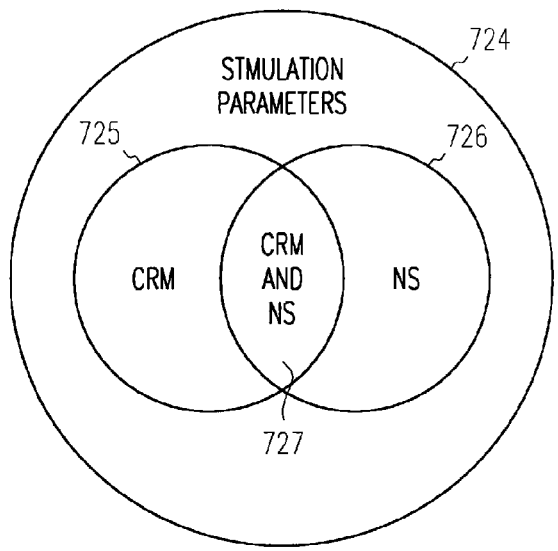
FIG. 7 illustrates a diagram, representing stimulation parameters, a region representing parameters capable of being used to perform CRM stimulation, a region representing parameters capable of being used to perform neural stimulation, and a region representing parameters capable of being used to perform both neural stimulation and CRM stimulation.

Parameters associated with neural stimulation signals include amplitude, frequency, burst frequency, pulse width, and morphology/waveform. FIG. 7 illustrates a diagram, representing stimulation parameters 724, a region 725 representing parameters capable of being used to perform CRM stimulation, a region 726 representing parameters capable of being used to perform neural stimulation, and a region 727 representing parameters capable of being used to perform both neural stimulation and CRM stimulation. Thus, FIG. 7 illustrates that some combinations of values for these parameters will result in both myocardial and neural stimulation, other combinations of values for these parameters will result in myocardial stimulation and not neural stimulation, and other combinations of values for these parameters will result in neural stimulation and not myocardial stimulation. Embodiments of the present subject matter adjust the stimulation parameters to selectively stimulate the myocardium, the nerve system, or both the myocardium and the nerve system.

Figure 8:
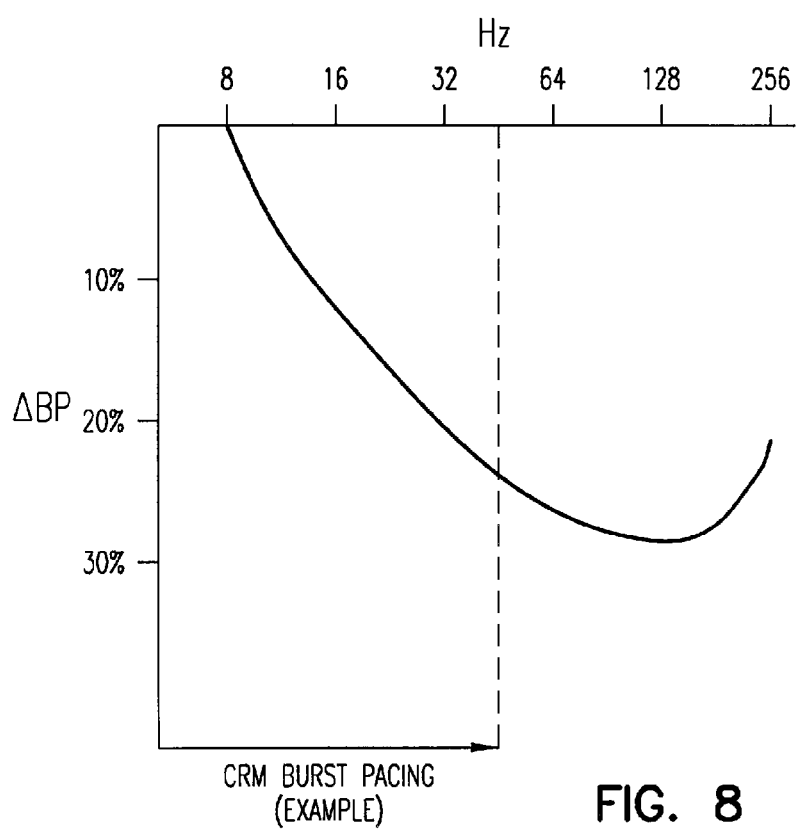
FIG. 8 is a graphical illustration of the relationship between a change in blood pressure and a rate of a stimulation signal.

For example, nerves are generally depolarized with a higher frequency signal than is typically used to capture myocardial tissue. FIG. 8 is a graphical illustration of the relationship between a change in blood pressure and a rate of a stimulation signal. The figure illustrates that the frequency of the stimulation signal significantly affects the decrease in blood pressure, which is a surrogate baroreflex parameter indicating the inhibition of SNA. The figure illustrates that a maximum decrease in blood pressure occurs at a stimulation frequency within a range from about 64 to about 256 Hz, and occurs approximately at 128 Hz. Some known CRM devices are capable of providing burst pacing capable of capturing myocardial tissue and at a frequency (e.g. 50 Hz) sufficient to elicit nerve depolarization. Various embodiments adjust the frequency, amplitude and/or morphology of the burst pacing according a stimulation mode to either stimulate the myocardia and not the nervous system, to stimulate both the myocardia and the nervous system, and to stimulate the nervous system but not the myocardia.

Various embodiments of pace or stimulator modules used in the implantable medical device of the present subject matter modulate the frequency of the stimulation signal to modulate the blood pressure to mimic the effects of a naturally-occurring pulse. Various embodiments stimulate with a frequency between approximately 8 Hz and approximately 512 Hz, or various ranges within this range such as approximately 16 Hz to approximately 128 Hz, approximately 32 Hz to approximately 128 Hz, for example. Other embodiments modulate other parameters of the stimulation signal to mimic the effects of the naturally-occurring pulse, and thus prevent or reduce adaptation to neural stimulation. By preventing the baroreflex from adapting to increased baroreflex activity, for example, long-term baroreflex stimulation can be used to achieve reflex reduction in hypertension. Varying the baroreflex stimulation maintains the reflex inhibition of SNA and abates (i.e. nullify or reduce in degree or intensity) adaptation to increased baroreflex activity that occurs during constant stimulation.

CRM Therapy

An example of CRM therapy is cardiac resynchronization therapy (CRT). However, CRM is not limited to CRT, as it includes a number of pacing modes and defibrillation modes. Clinical data has shown that cardiac resynchronization therapy (CRT), achieved through synchronized biventricular pacing, results in a significant improvement in cardiac function. It has also been reported CRT can be beneficial in preventing and/or reversing the ventricular remodeling that often occurs in post-MI and heart failure patients. The combined application of remodeling control therapy (RCT) by controlling ventricular activation with cardiac resynchronization pacing and anti-remodeling therapy (ART) by stimulating the baroreflex in order to inhibit sympathetic activity provides a greater therapeutic benefit than either of them individually. The device controls ventricular activation through synchronized pacing of the right and left ventricles. In addition, the device may provide a combination of parasympathetic stimulation and sympathetic inhibition. Parasympathetic stimulation can be achieved through a nerve cuff electrode placed around the cervical vagus nerve bundle, while sympathetic inhibition can be achieved through baroreflex stimulation, either through a nerve cuff electrode placed around the aortic or carotid sinus nerve, or though a stimulation lead designed to stimulate baroreceptors in the pulmonary artery. The device controls the delivery of RCT and ART independently in either an open-loop or closed-loop fashion, the latter based upon a cardiac function assessment performed by the device.

Implantable cardiac devices that provide electrical stimulation to selected chambers of the heart have been developed in order to treat a number of cardiac disorders. A pacemaker, for example, is a device which paces the heart with timed pacing pulses, most commonly for the treatment of bradycardia where the ventricular rate is too slow. Atrio-ventricular conduction defects (i.e., AV block) and sick sinus syndrome represent the most common causes of bradycardia for which permanent pacing may be indicated. If functioning properly, the pacemaker makes up for the heart's inability to pace itself at an appropriate rhythm in order to meet metabolic demand by enforcing a minimum heart rate. Implantable devices may also be used to treat cardiac rhythms that are too fast, with either anti-tachycardia pacing or the delivery of electrical shocks to terminate atrial or ventricular fibrillation.

Implantable devices have also been developed that affect the manner and degree to which the heart chambers contract during a cardiac cycle in order to promote the efficient pumping of blood. The heart pumps more effectively when the chambers contract in a coordinated manner, a result normally provided by the specialized conduction pathways in both the atria and the ventricles that enable the rapid conduction of excitation (i.e., depolarization) throughout the myocardium. These pathways conduct excitatory impulses from the sino-atrial node to the atrial myocardium, to the atrio-ventricular node, and thence to the ventricular myocardium to result in a coordinated contraction of both atria and both ventricles. This both synchronizes the contractions of the muscle fibers of each chamber and synchronizes the contraction of each atrium or ventricle with the contralateral atrium or ventricle. Without the synchronization afforded by the normally functioning specialized conduction pathways, the heart's pumping efficiency is greatly diminished. Pathology of these conduction pathways and other inter-ventricular or intra-ventricular conduction deficits can be a causative factor in heart failure, which refers to a clinical syndrome in which an abnormality of cardiac function causes cardiac output to fall below a level adequate to meet the metabolic demand of peripheral tissues. In order to treat these problems, implantable cardiac devices have been developed that provide appropriately timed electrical stimulation to one or more heart chambers in an attempt to improve the coordination of atrial and/or ventricular contractions, termed cardiac resynchronization therapy (CRT). Ventricular resynchronization is useful in treating heart failure because, although not directly inotropic, resynchronization can result in a more coordinated contraction of the ventricles with improved pumping efficiency and increased cardiac output. Currently, a common form of CRT applies stimulation pulses to both ventricles, either simultaneously or separated by a specified biventricular offset interval, and after a specified atrio-ventricular delay interval with respect to the detection of an intrinsic atrial contraction or delivery of an atrial pace.

It has also been found that CRT can be beneficial in reducing the deleterious ventricular remodeling which can occur in post-MI and heart failure patients. Presumably, this occurs as a result of changes in the distribution of wall stress experienced by the ventricles during the cardiac pumping cycle when CRT is applied. The degree to which a heart muscle fiber is stretched before it contracts is termed the preload, and the maximum tension and velocity of shortening of a muscle fiber increases with increasing preload. When a myocardial region contracts late relative to other regions, the contraction of those opposing regions stretches the later contracting region and increases the preload. The degree of tension or stress on a heart muscle fiber as it contracts is termed the afterload. Because pressure within the ventricles rises rapidly from a diastolic to a systolic value as blood is pumped out into the aorta and pulmonary arteries, the part of the ventricle that first contracts due to an excitatory stimulation pulse does so against a lower afterload than does a part of the ventricle contracting later. Thus a myocardial region which contracts later than other regions is subjected to both an increased preload and afterload. This situation is created frequently by the ventricular conduction delays associated with heart failure and ventricular dysfunction due to an MI. The increased wall stress to the late-activating myocardial regions is most probably the trigger for ventricular remodeling. By pacing one or more sites in a ventricle in a manner which causes a more coordinated contraction, CRT provides pre-excitation of myocardial regions which would otherwise be activated later during systole and experience increased wall stress. The pre-excitation of the remodeled region relative to other regions unloads the region from mechanical stress and allows reversal or prevention of remodeling to occur.

Neural Stimulation Therapies

One neural stimulation therapy involves treating hypertension by stimulating the baroreflex for sustained periods of time sufficient to reduce hypertension. Another therapy involves preventing and/or treating ventricular remodeling. Activity of the autonomic nervous system is at least partly responsible for the ventricular remodeling which occurs as a consequence of an MI or due to heart failure. It has been demonstrated that remodeling can be affected by pharmacological intervention with the use of, for example, ACE inhibitors and beta-blockers. Pharmacological treatment carries with it the risk of side effects, however, and it is also difficult to modulate the effects of drugs in a precise manner. Embodiments of the present subject matter employ electrostimulatory means to modulate autonomic activity, referred to as anti-remodeling therapy or ART. When delivered in conjunction with ventricular resynchronization pacing, such modulation of autonomic activity acts synergistically to reverse or prevent cardiac remodeling.

Increased sympathetic nervous system activity following ischemia often results in increased exposure of the myocardium to epinephrine and norepinephrine. These catecholamines activate intracellular pathways within the myocytes, which lead to myocardial death and fibrosis. Stimulation of the parasympathetic nerves (vagus) inhibits this effect. According to various embodiments, the present subject matter selectively activates the vagal cardiac nerves in addition to CRT in heart failure patients to protect the myocardium from further remodeling and arrhythmogenesis. Other potential benefits of stimulating vagal cardiac nerves in addition to CRT include reducing inflammatory response following myocardial infarction, and reducing the electrical stimulation threshold for defibrillating. For example, when a ventricular tachycardia is sensed, vagal nerve stimulation is applied, and then a defibrillation shock is applied. The vagal nerve stimulation allows the defibrillation shock to be applied at less energy.

Figure 9A:
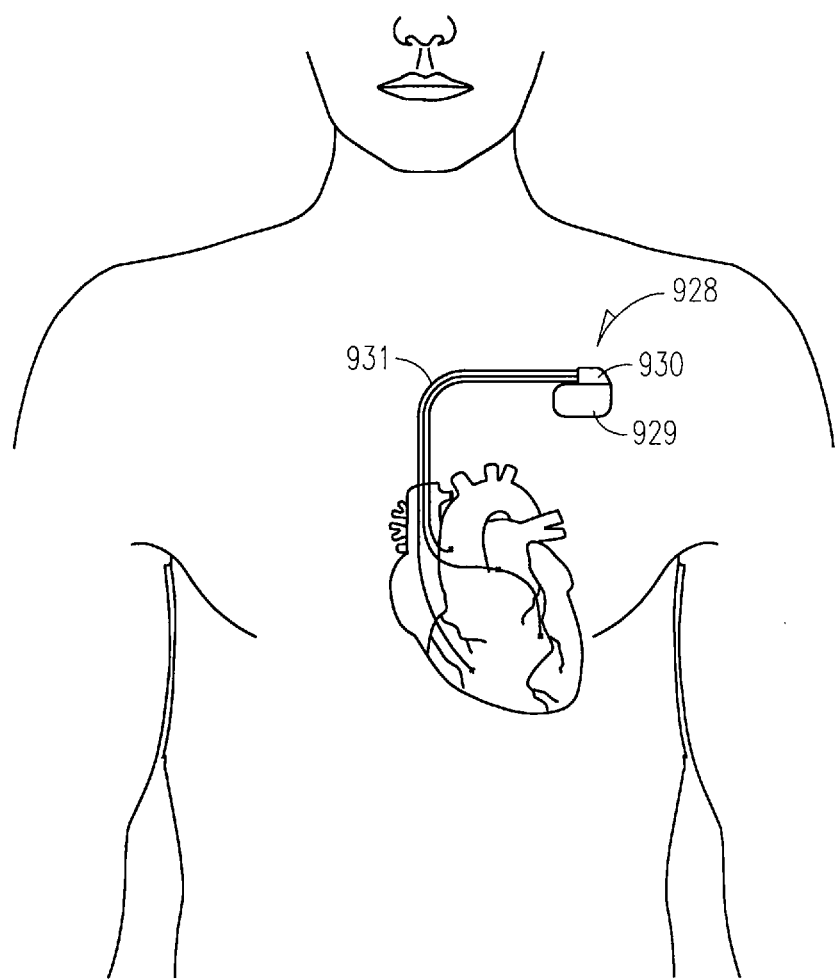
FIG. 9A illustrates an implantable medical device with leads extending into a heart.
Figure 9C:
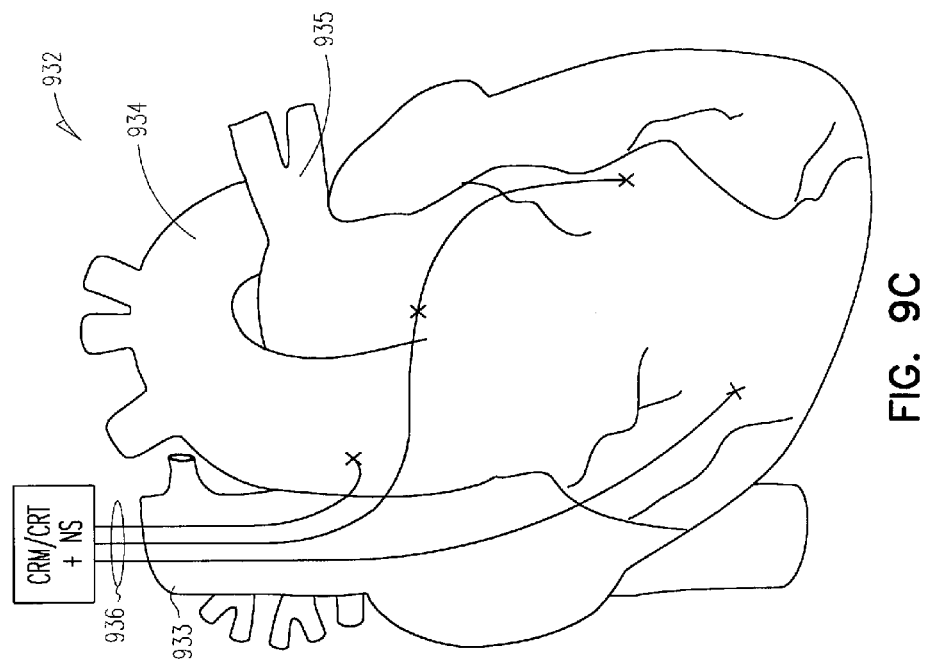
FIGS. 9B and 9C illustrate an implantable medical device with endocardial and epicardial leads, respectively.
Figure 9B:
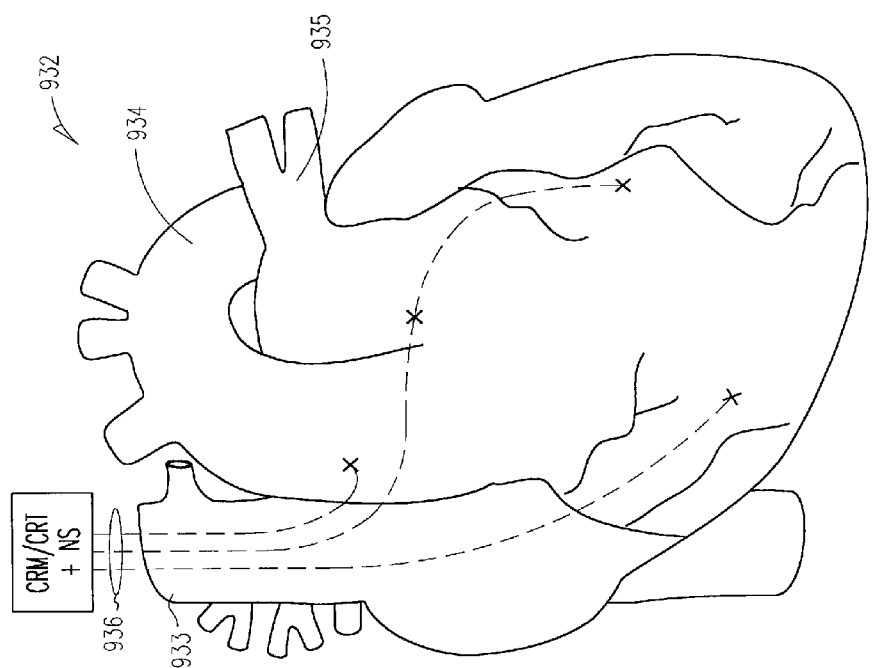

FIG. 9A illustrates an implantable medical device (IMD) with leads extending into a heart; and FIGS. 9B and 9C illustrate an implantable medical device with endocardial and epicardial leads, respectively. FIG. 9A illustrates the IMD 928, including a pulse generator 929 and a header 930. Leads 931 are attached to the header and are appropriately guided to place electrodes on the lead in position to provide the desired stimulation response.

As illustrated in FIGS. 9B and 9C, the heart 932 includes a superior vena cava 933, an aortic arch 934, and a pulmonary artery 935. CRM leads 936 pass nerve sites that can be stimulated in accordance with the present subject matter. FIG. 9B illustrates transvascularly fed leads, and FIG. 9C illustrates epicardial leads. Examples of electrode positions are provided in the drawings by the symbol "X". For example, CRM leads are capable of being intravascularly inserted through a peripheral vein and into the coronary sinus, and are capable of being intravascularly inserted through a peripheral vein and through the tricuspid valve into the right ventricle of the heart (not expressly shown in the figure) similar to a cardiac pacemaker lead, and continue from the right ventricle through the pulmonary valve into the pulmonary artery. The coronary sinus and pulmonary artery are provided as examples of vasculature proximate to the heart in which a lead can be intravascularly inserted to stimulate nerves within or proximate to the vasculature. Thus, according to various aspects of the present subject matter, nerves are stimulated in or around vasculature located proximate to the heart by at least one electrode intravascularly inserted therein.

Figure 10B:
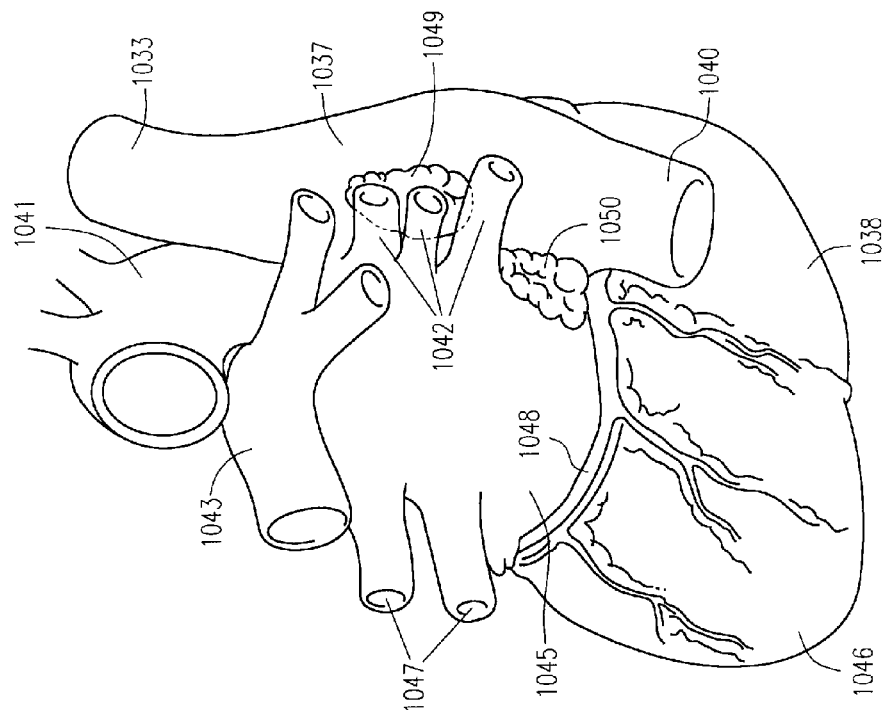
FIGS. 10A and 10B illustrate the right side and left side of the heart, respectively, and further illustrate cardiac fat pads which provide neural targets for some neural stimulation therapies.
Figure 10A:
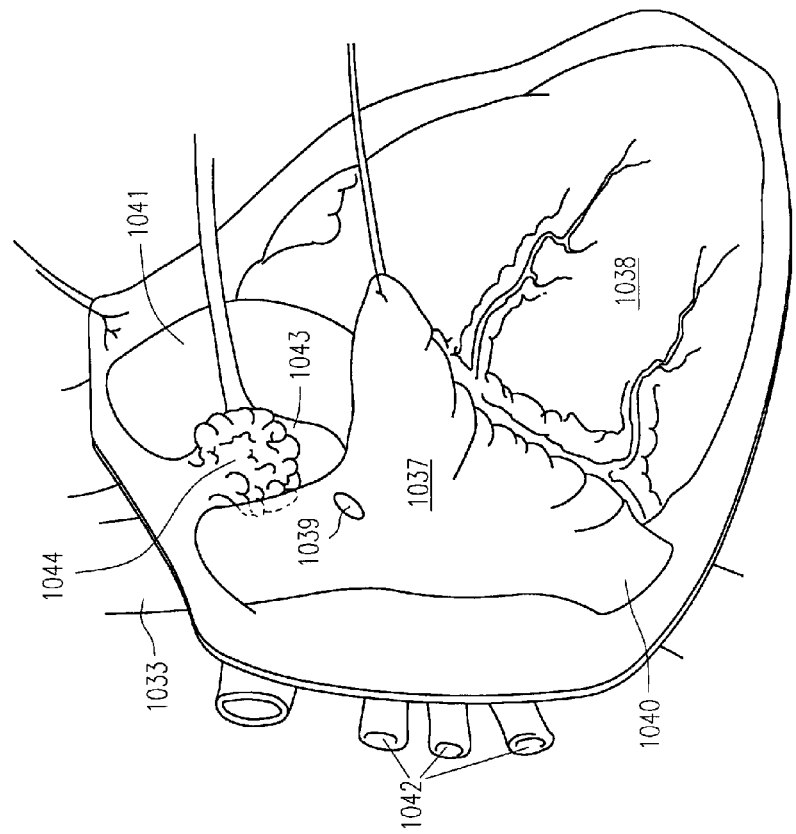

FIGS. 10A and 10B illustrate the right side and left side of the heart, respectively, and further illustrate cardiac fat pads which provide neural targets for some neural stimulation therapies. FIG. 10A illustrates the right atrium 1037, right ventricle 1038, sinoatrial node 1039, superior vena cava 1033, inferior vena cava 1040, aorta 1041, right pulmonary veins 1042, and right pulmonary artery 1043. FIG. 10A also illustrates a cardiac fat pad 1044 between the superior vena cava and aorta. Neural targets in the cardiac fat pad 1044 are stimulated in some embodiments using an electrode screwed into or otherwise placed in the fat pad, and are stimulated in some embodiments using an intravenously-fed lead proximately positioned to the fat pad in a vessel such as the right pulmonary artery or superior vena cava, for example. FIG. 10B illustrates the left atrium 1045, left ventricle 1046, right atrium 1037, right ventricle 1038, superior vena cava 1033, inferior vena cava 1040, aorta 1041, right pulmonary veins 1042, left pulmonary vein 1047, right pulmonary artery 1043, and coronary sinus 1048. FIG. 10B also illustrates a cardiac fat pad 1049 located proximate to the right cardiac veins and a cardiac fat pad 1050 located proximate to the inferior vena cava and left atrium. Neural targets in the fat pad 1049 are stimulated in some embodiments using an electrode screwed into the fat pad 1049, and are stimulated in some embodiments using an intravenously-fed lead proximately positioned to the fat pad in a vessel such as the right pulmonary artery 1043 or right pulmonary vein 1042, for example. Neural targets in the fat pad 1050 are stimulated in some embodiments using an electrode screwed into the fat pad, and are stimulated in some embodiments using an intravenously-fed lead proximately positioned to the fat pad in a vessel such as the inferior vena cava 1040 or coronary sinus or a lead in the left atrium 1045, for example.

In various embodiments, a neural stimulation channel uses a lead adapted to be intravascularly disposed to transvascularly stimulate an appropriate nerve, e.g., near a baroreceptor to provide a sympathetic inhibition or near a parasympathetic nerve to provide parasympathetic stimulation. Some CRT devices include an atrial lead to pace and/or sense the right atrium, a right ventricle lead to pace and/or sense the right ventricle, and a left ventricle lead fed through the coronary sinus to a position to pace and/or sense the left ventricle, such as illustrated in FIGS. 9B and 9C. A lead within the coronary sinus is capable of being used to transvascularly stimulate target parasympathetic nerves anatomically located on the extravascular surface of the coronary sinus at a strength sufficient to elicit depolarization of adjacent nerves, and is also capable of being used to deliver cardiac resynchronization therapy with appropriately timed pacing pulses at a site proximate to the left ventricle, for example.

Various lead embodiments implement a number of designs, including an expandable stent-like electrode with a mesh surface dimensioned to abut a wall of a predetermined blood vessel, a coiled electrode(s), a fixed screw-type electrode(s), and the like. Various embodiments place the electrode(s) inside the blood vessel, into the wall of the blood vessel, or a combination of at least one electrode inside the blood vessel and at least one electrode into the wall of the blood vessel. The neural stimulation electrode(s) can be integrated into the same lead used for CRT or in another lead in addition to CRT lead(s).

Intravascularly-fed leads adapted to transvascularly stimulate a target outside of the vessel, also referred to herein as transvascular leads, can be used to stimulate other nerve sites. For example, an embodiment feeds a transvascular stimulation lead into the right azygos vein to stimulate the vagus nerve; and an embodiment feeds a transvascular stimulation lead into the internal jugular vein to stimulate the vagus nerve. Various embodiments use at least one lead intravascularly fed along a lead path to transvascularly apply neural stimulation and electrically stimulate a cardiac muscle, such as ventricular pacing, as part of CRT.

Other transvascular locations have been mentioned with respect to FIGS. 10A and 10B. Depending on the intravascular location of the neural stimulation electrode(s), the right vagal branch, the left vagal branch or a combination of the right and left vagal branches are capable of being stimulated.

The left and right vagal branches innervate different areas of the heart, and thus provide different results when stimulated. According to present knowledge, the right vagus nerve appears to innervate the right side of the heart, including the right atrium and right ventricle, and the left vagus nerve appears to innervate the left side of the heart, including the left atrium and left ventricle. Stimulation of the right vagus has more chronotropic effects because the sinus node is on the right side of the heart. Thus, various embodiments selectively stimulate the right vagus nerve and/or the left vagus nerve to selectively control contractility, excitability, and inflammatory response on the right and/or left side of the heart. Since the venous system is for the most part symmetrical, leads can be fed into an appropriate vessel to transvascularly stimulate the right or left vagus nerve. For example, a lead in the right internal jugular vein can be used to stimulate the right vagus nerve and a lead in the left internal jugular vein can be used to stimulate the left vagus nerve.

The stimulation electrode(s) are not in direct neural contact with the nerve when the transvascular approach to peripheral nerve stimulation is used. Thus, problems associated with neural inflammation and injury commonly associated with direct contact electrodes are reduced.

In an embodiment of the invention, an implantable device for delivering cardiac therapy to post-MI patients includes one or more pacing channels for delivering pacing pulses to one or more ventricular sites and a neural stimulation channel for stimulating nerves. The controller is programmed to deliver remodeling control therapy (RCT) by delivering ventricular pacing in a cardiac resynchronization mode which pre-excites a region of the ventricular myocardium so as to mechanically unload that region during systole. The cardiac resynchronization therapy may be delivered as biventricular pacing where one of the ventricles is pre-excited relative to the other as determined by a programmed biventricular offset interval. In an embodiment in which patients suffer from delayed activation of the left ventricle, a left ventricle-only resynchronization pacing mode is employed. In another embodiment, the pacing therapy may be delivered as multi-site ventricular pacing where at least one of the ventricles is paced at a plurality of sites so as to pre-excite one or more of the sites relative to the other sites. In any case, the ventricular pacing may be delivered in a non-atrial tracking mode where a ventricular escape interval is defined between ventricular paces, or in an atrial tracking mode where the ventricular paces are delivered after a defined atrio-ventricular escape interval following an atrial sense. In a patient who is chronotropically incompetent, an atrial pacing channel may also be provided for pacing the atria, with the ventricular pace(s) delivered upon expiration of the atrio-ventricular escape interval following the atrial pace.

The controller is further programmed to deliver anti-remodeling therapy (ART) in conjunction with the RCT using a lead incorporating an electrode adapted for disposition near an arterial baroreceptor or afferent nerve of a baroreflex arc. Stimulation of the baroreflex arc results in inhibition of sympathetic activity. The electrode may be intravascularly positioned in a blood vessel or elsewhere proximate to a baroreceptor or afferent nerve such as in a pulmonary artery or a cardiac fat pad. In another embodiment, the device delivers the anti-remodeling therapy by stimulating parasympathetic nerve activity. The electrode may be a nerve cuff electrode adapted for disposition around a parasympathetic nerve or an intravascular electrode for transvascularly stimulating a parasympathetic nerve adjacent to a blood vessel.

The device may be programmed to deliver RCT and ART in open-loop fashion where the RCT and ART are delivered simultaneously or separately at programmed intervals. In another embodiment, the device is programmed to deliver RCT and ART in closed-loop fashion, where the intensities of RCT and ART are modulated in accordance with an assessment of cardiac function performed by the controller.

The device may also separately modulate the intensities of parasympathetic stimulation and sympathetic inhibition which are delivered as part of the ART in accordance with the assessment of cardiac function. Cardiac function may be assessed by the device using several different modalities, either alone or in combination. In one embodiment, the device incorporates a sensor for measuring cardiac output, and the controller is programmed to modulate the delivery of RCT and ART in accordance with the measured cardiac output. As described above, such a cardiac output sensor may be a transthroracic impedance measuring circuit. A means for assessing cardiac function is an arterial blood pressure sensor, where the controller is programmed to modulate the delivery of RCT and ART in accordance with the measured blood pressure. The blood pressure sensor may take the form of a pressure transducer and lead adapted for disposition within an artery. A measure of the patient's respiratory activity taken by a minute ventilation sensor may be used as a surrogate for blood pressure. Cardiac function may also be assessed by measuring the patient's exertion level (e.g., using either a minute ventilation sensor or an accelerometer) together with a measure of cardiac output and/or blood pressure, where the controller is then programmed to modulate the delivery of RCT and ART in accordance with the combined measurements.

In an embodiment, the cardiac function assessment includes an assessment of the patient's autonomic balance. Autonomic balance may be assessed directly with a sensing channel for measuring electrical activity in sympathetic and parasympathetic nerves with appropriately positioned sensing electrodes, or if the patient is chronotropically competent, by measuring the intrinsic heart rate. As described above, measuring heart rate variability provides one means for assessing autonomic balance. Thus, the device may include circuitry for measuring and collecting time intervals between successive intrinsic beats, referred to as a BB interval, where the BB interval may be an interval between successive atrial or ventricular senses. The device stores the collected intervals as a discrete BB interval signal, filters the BB interval signal into defined high and low frequency bands, and determines the signal power of the BB interval signal in each of the low and high frequency bands, referred to LF and HF, respectively. The device then computes an LF/HF ratio and assesses autonomic balance by comparing the LF/HF ratio to a specified threshold value.

Implantable Medical Device

Figure 11:
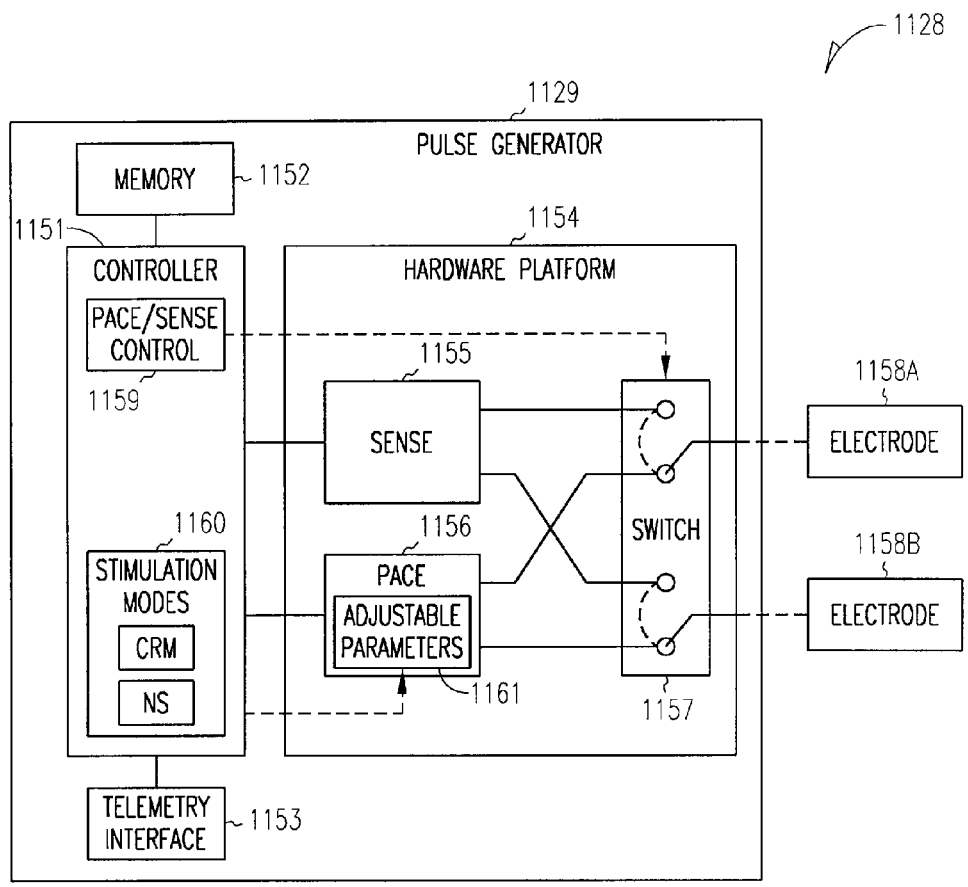
FIG. 11 illustrates an embodiment of an implantable medical device.

Neural stimulation as described herein may be delivered by an implantable medical device configured to deliver only neural stimulation or to deliver other therapies such as bradycardia and/or cardiac resynchronization pacing, anti-tachyarrhythmia therapies such as cardioversion/defibrillation and/or anti-tachycardia pacing, and/or other therapies. An implantable device for delivering neural stimulation may also incorporate one or more sensing channels for sensing cardiac electrical activity and/or other physiological parameters. FIG. 11 illustrates one embodiment of an implantable medical device 1128 for delivering neural stimulation. The illustrated device includes a pulse generator 1129, and the pulse generator includes a controller 1151 to communicate with a memory 1152, a telemetry interface 1153 for use in communicating with a programmer (not illustrated) of the implantable medical device, and a stimulating/sensing hardware platform 1154. The illustrated hardware platform includes a sense module 1155, a pace module 1156, and switches 1157 for use to operably connect the sense module and the pace module to the electrodes 1158A and 1158B. The illustrated electrodes can be two electrodes on one lead, such as a tip and ring electrode or can be on separate leads. Additionally, one of the electrodes can be a conductive portion, also referred to as a "can", of the implantable medical device. The illustrated controller 1151 includes a pace/sense control module 1159 to control the switches and selectively enable the sense module to operably connect to the electrodes and sense a potential across the electrodes or the pace module to operably connect to the electrodes and apply a pacing signal to generate a pacing potential between the electrodes to provide a desired electrical stimulus to a patient.

The illustrated controller 1151 includes a stimulation mode module 1160, and the illustrated pace module includes adjustable parameters 1161, such as, for example, amplitude, frequency, waveform, and pacing mode. The parameters of the pace module are able to be adjusted to selectively provide a neural stimulation signal to the electrodes or a myocardial stimulation signal to the electrodes. In some embodiments, the parameters are able to be adjusted to selectively apply a neural stimulation signal adapted to simultaneously provide myocardial and neural stimulation. According to various embodiments, the stimulation mode module is adapted to selectively apply CRM or myocardial stimulation using the electrodes, neural stimulation using the electrodes, selectively alternate between myocardial and neural stimulation using the electrodes according to a desired therapy, and/or simultaneously apply both myocardial and neural stimulation using the electrodes. The illustrated pace module includes adjustable parameters.

Figure 12:
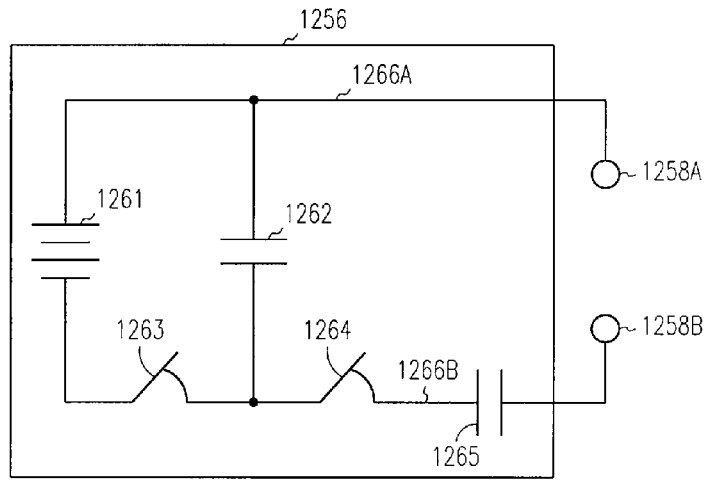
FIG. 12 is a simplified schematic illustration of a pace module for the hardware platform illustrated in FIG. 11.

FIG. 12 is a simplified schematic illustration of a pace module 1256 for the hardware platform illustrated in FIG. 11. The illustrated pace module includes a connection to a power supply 1261 (e.g. the battery of the implantable medical device), a pacing capacitor 1262, a charge switch 1263 and a discharge switch 1264. The charge switch is closed and the discharge switch is opened when a charge is being stored from the power supply onto the pacing capacitor, and the charge switch is opened and the discharge switch is closed to discharge the pacing capacitor as a pacing signal across the electrodes 1258A and 1258B. Some embodiments include a discharge capacitor 1265 in series with the discharge circuit to attenuate the polarization voltages or after potentials which follow the application of a stimulation pulse to allow the sensing module to sense an intrinsic potential between the electrodes. Additional circuitry can be added to control and selectively adjust the potential across a charged capacitor, to adjust the duration and attenuation of a discharge signal, to adjust the waveform or morphology of the discharge signal, to adjust the frequency of the discharge signal, and to provide burst pacing, for example. Those of ordinary skill in the art, upon reading and comprehending this disclosure, would understand how to design a pace module to provide these adjustable parameters and incorporate the pace modules in a design of an implantable medical device to allow the controller to selectively apply a signal to stimulate heart muscle, a signal to stimulate a neural response, and in some embodiments, a stimulation signal to provide both myocardial and neural stimulation.

The device illustrated in FIG. 12 shows a simplified device with signal paths 1266A and 1266B to two electrodes. Each signal path used to apply a stimulation signal and used to sense a stimulation signal can be referred to as a channel. The implantable medical device can be designed with switches to selectively connect one or more electrodes to each channel, or the implantable the electrode(s) can be designed such that each channel is connected to predetermined electrode(s). Each channel is capable of being individually controlled to send a stimulation signal to a predetermined electrode(s).

Figure 13:
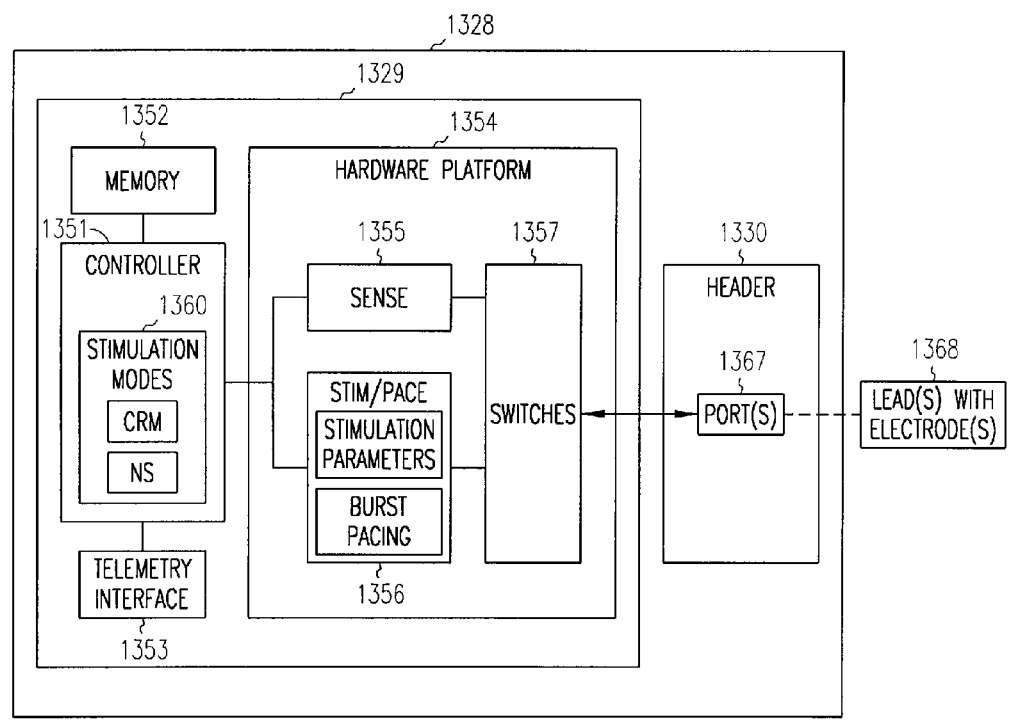
FIG. 13 illustrates a multi-channel embodiment of an implantable medical device.

FIG. 13 illustrates a multi-channel embodiment of an implantable medical device. The illustrated device 1328 includes a pulse generator 1329, and the pulse generator includes a controller 1351 to communicate with a memory 1352, a telemetry interface 1353 for use in communicating with a programmer of the implantable medical device, and a hardware platform 1354. The illustrated hardware platform includes a sense module 1355, a stimulation or pace module 1356, and switches 1357 for use to operably connect the sense module and the pace module to a header 1330. The header includes one or more ports 1367 to receive a lead 1368. Each lead can include one or more electrodes. The switches selectively provide desired connections between the sense and pace modules and the ports in the header to provide desired pace channels between the pace module and desired electrode(s) on the lead(s), and to provide desired sense channels between the sense module and desired electrode(s) on the lead(s). In various embodiments, the can of the implantable medical device is used as an electrode. Some embodiments of the pace module 1356 include circuitry to independently and simultaneously provide stimulation signals on multiple channels.

The controller includes a pace/sense control module to control the switches and selectively enable the sense module to operably connect to the electrodes and sense a potential across the electrodes or the pace module to operably connect to the electrodes and apply a pacing signal to generate a pacing potential between the electrodes to provide a desired electrical stimulus to a patient.

The illustrated controller includes a stimulation mode module 1360, and the illustrated pace module 1356 includes adjustable stimulation parameters, including burst pacing parameters. The parameters of the pace module are able to be adjusted to selectively provide a neural stimulation signal to selected electrodes or a myocardial stimulation signal to selected electrodes. In some embodiments, the stimulation parameters of the pace module are able to be adjusted to selectively apply a neural stimulation signal adapted to simultaneously provide myocardial and neural stimulation. According to various embodiments, the stimulation mode module is adapted to selectively apply CRM or myocardial stimulation using the electrodes, neural stimulation using the electrodes, selectively alternate between myocardial and neural stimulation using the electrodes according to a desired therapy, and/or simultaneously apply both myocardial and neural stimulation using the electrodes.

The present subject matter is capable of providing neural and CRM stimulation therapies over one stimulation channel. Some embodiments involve operating a CRM hardware platform, designed to capture heart muscle, in a mode with stimulation parameters selected to depolarize nerves. For example, the CRM hardware platform may be operated in a burst pacing mode with a relatively low amplitude and a relatively high frequency to provide neural stimulation.

Certain stimulation channels can be programmed to be dedicated to either CRM pacing or neural stimulation. In some embodiments, the stimulation channels are able to intermittently and distinctly perform CRM pacing and neural stimulation. The different stimulation modes are performed at different times, such as can be done with a time domain multiplexing of the stimulation channel. In some embodiments, the stimulation channels are able to transmit a stimulation signal to simultaneously stimulate the heart muscle and a desired neural response. For example, a higher frequency neural stimulation signal can be modulated on a lower frequency CRM stimulation signal.

Figure 15:
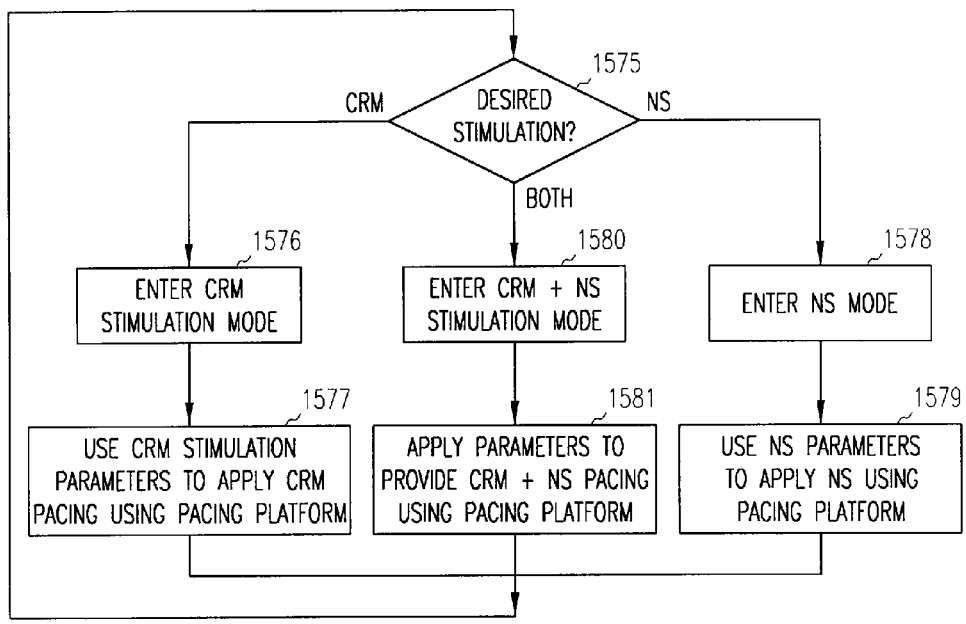
FIG. 15 illustrates a method to selectively provide myocardial and/or neural stimulation over a stimulation channel of the implantable medical device.

FIG. 15 illustrates a method to selectively provide myocardial and/or neural stimulation over a stimulation channel of the implantable medical device. In the illustrated method, the desired stimulation is determined at 1575. If CRM stimulation is desired, the process proceeds to 1576 and the device enters a CRM stimulation mode. As represented at 1577, CRM stimulation parameters are used to apply CRM according to appropriate CRM algorithms using a pacing hardware platform. If, at 1575, it is determined that it is desired to provide neural stimulation therapy, the process proceeds to 1578 to enter a neural stimulation. As represented at 1579, neural stimulation parameters are used to apply neural stimulation according to appropriate algorithms using the pacing hardware platform, which is the same platform used to provide CRM stimulation. According to some embodiments, if at 1575 it is desired to simultaneously provide both CRM and neural stimulation, the process proceeds to 1580 where the devices enters a CRM and NS mode. As represented at 1581, parameters are used to apply a stimulation signal to provide both CRM and NS pacing using the pacing platform of the device.

Lead Arrangements

The leads can be placed in a number of physiological locations. Some examples have been provided above. An implantable device embodiment contains one or more myocardial stimulation leads, as well as one or more neural leads. Examples of neural stimulation leads include an expandable stimulation lead, such as a stent-like lead, placed in the pulmonary artery in the proximity of a high concentration of baroreceptors; a transvascular lead placed proximal to one of the cardiac fat pads, or an epicardial lead placed in the cardiac fat pad; and a cuff electrode placed around a nerve trunk, such as the aortic, carotid or vagus nerve.

In an embodiment, myocardial stimulation and neural stimulation are provided using the same lead(s) using different electrodes on the lead(s) or using the same electrodes on the lead(s). In some embodiments, the same lead can be used to simultaneously provide neural stimulation and myocardial stimulation or to provide neural stimulation and to provide myocardial stimulation at different times than the neural stimulation. In some embodiments, the leads are dedicated to either neural stimulation or stimulation of myocardial tissue. In embodiments that use dedicated leads, the controller of the implantable medical device is able to select the stimulation mode for the pace channel to the dedicated lead, and does not alternate between CRM and neural stimulation modes.

Neural Stimulation Circuitry and Waveforms

The present subject matter provides a hardware platform that is capable of providing neural stimulation alone or in combination with CRM/myocardial stimulation. CRM therapy typically uses pacing signals with a relatively larger amplitude and lower frequency than neural stimulation signals, and the stimulation parameters can be appropriately adjusted for a desired stimulation mode. Some stimulation signals have parameters sufficient for both CRM/myocardial stimulation and neural stimulation. Thus, some embodiments of the present subject matter provide a mode to provide simultaneous CRM and neural stimulation. For example, a CRM stimulation waveform can be designed to have harmonic frequencies capable of stimulating nervous system.

Figure 14A:
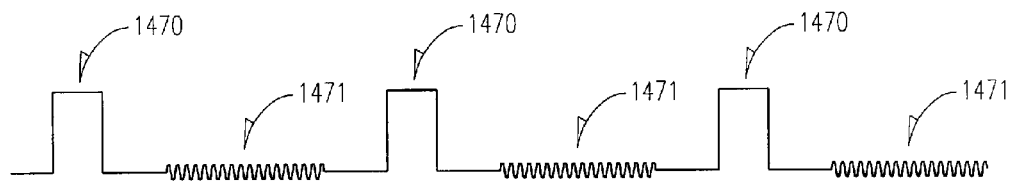
FIGS. 14A, 14B and 14C illustrate examples of waveforms used to provide myocardial and neural stimulation.
Figure 14B:
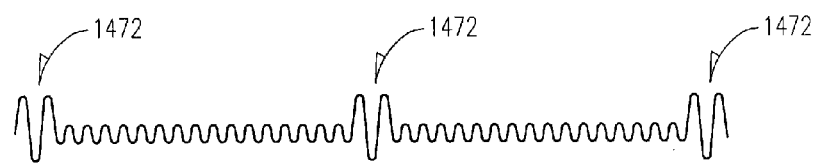
Figure 14C:
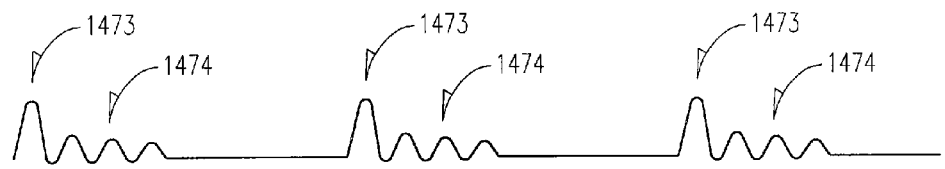

FIGS. 14A, 14B and 14C illustrate examples of waveforms used to provide myocardial and neural stimulation. FIG. 14A illustrates a stimulation waveform applied between at least two electrodes that alternates between a CRM stimulation pulse 1470 and a neural stimulation 1471, which is illustrated as a higher frequency signal. The CRM stimulation and neural stimulation need not alternate, as some embodiments apply the CRM and/or neural stimulation only as a as-needed bases according to a closed-loop feedback of sensed physiological parameter(s) (e.g. demand pacing for CRM stimulation, and sensed blood pressure for neural stimulation). In such embodiments, a time domain multiplexing scheme is used, where any CRM stimulation to be applied is provided in one portion of a timing period and any neural stimulation to be applied is provided in another portion of the timing period.

FIG. 14B illustrates another stimulation waveform applied between at least two electrodes. The illustrated waveform illustrates an example of simultaneous myocardial and neural stimulation. The waveform has a signal frequency sufficient to elicit depolarization of nerves. The amplitude of the signal increases to a potential sufficient to capture heart muscle, such as illustrated at 1472.

FIG. 14C illustrates another waveform applied between at least two electrodes. The illustrated waveform provides CRM stimulation pulses with an amplitude sufficient to capture heart muscle. The CRM stimulation signal attenuates after the heart muscle is captured at 1473 to provide neural stimulation 1474 on the same electrodes.

In some embodiments, the stimulation channel is designated during programming to either provide CRM or neural stimulation. In some embodiments, the stimulation channel is designated to either provide CRM or neural stimulation during the assembly of the implantable device via hardwiring, software, or logic circuits.

In one particular embodiment, the stimulation circuitry is configured to deliver a waveform for neural stimulation with the following approximate parameters:
  frequency=20 Hz
  pulse width=300 us
  amplitude=1.5-2.0 mA
This waveform can be delivered as a pulse train applied either continuously or intermittently (e.g., with a duty cycle=10 sec ON, 50 sec OFF) in order to provide, for example, anti-remodeling therapy to post-MI or heart failure patients. Such stimulation may be applied either chronically or periodically in accordance with lapsed time intervals or sensed physiological conditions. This waveform has been demonstrated in pre-clinical studies to be a particularly effective anti-remodeling therapy when applied to the vagus nerve in the cervical region, where the stimulation may be applied through either a nerve cuff or a transvascular lead. The stimulating configuration for delivering the waveform may be any of the configurations described in this document such as either a bipolar configuration or a unipolar configuration with a far-field subcutaneous return electrode. The stimulation circuitry may be either dedicated to delivering neural stimulation or may be configured to also deliver waveforms suitable for CRM.

Figure 16:
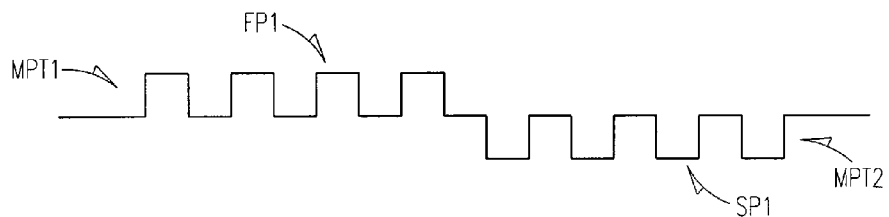
FIG. 16 illustrates a waveform made up of monophasic pulse trains with alternating polarity as would be generated by a current source pulse output circuit.
Figure 17:
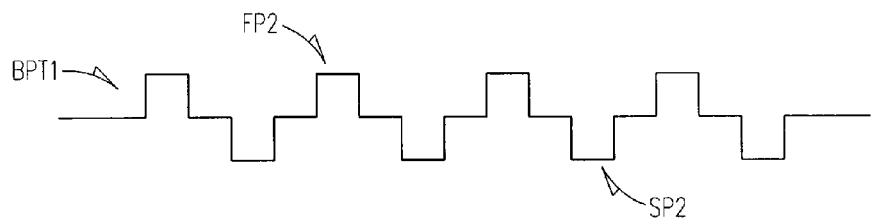
FIG. 17 illustrates a biphasic waveform with alternating polarity as would be generated by a current source pulse output circuit.

In another embodiment, a neural stimulation waveform such as described in the preceding paragraph or elsewhere in this document may be delivered with phases of alternating polarity, referred to herein as first and second phases. For example, the waveform may be delivered as monophasic pulses with a bipolar stimulating configuration and with a "bipolar switch" so that the phase of the monophasic pulses is alternated in each consecutive pulse train. That is, a pulse train with monophasic pulses having first phases of one polarity is then followed by a pulse train with monophasic pulses having second phases of the opposite polarity. FIGS. 16 and 17 show example waveforms as would be produced by recording the potential between the stimulation electrodes. FIG. 16 shows an example of such a waveform in which a monophasic pulse train MPT1 having first phases FP1 of positive polarity is followed by a monophasic pulse train MPT2 having second phases SP1 of negative polarity. In another embodiment, the stimulation circuitry may be configured to deliver a pulse train with biphasic pulses so that the first phase alternates with the second phase (i.e., each consecutive pulse in the train alternates in polarity). FIG. 17 shows an example of a biphasic pulse train BPT1 having first phases FP2 and second phases SP2 that alternate in polarity. Such biphasic pulse trains with alternating polarities or a series of monophasic pulses trains having alternating polarities may be applied continuously or on a periodic or intermittent basis for a specified period of time.

Figure 20:
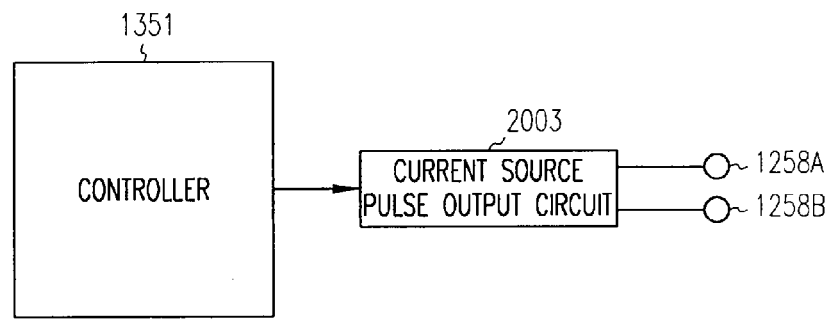
FIG. 20 illustrates an embodiment of circuitry for delivering stimulation pulse trains using a current source pulse output circuit.
Figure 21:
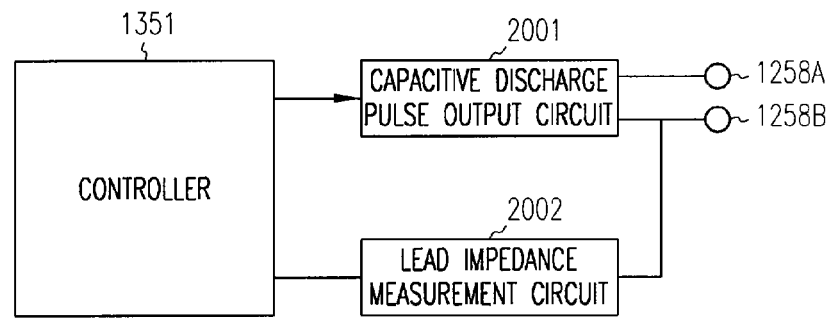
FIG. 21 illustrates an embodiment of circuitry for delivering stimulation pulse trains using a capacitive discharge pulse output circuit.

FIGS. 20 and 21 illustrate different embodiments of circuitry for delivering stimulation pulse trains as described above. In FIG. 20, a current source pulse output circuit 2003 outputs current pulses between stimulation electrodes 1258A and 1258B in accordance with command inputs from the controller 1351. The command inputs from the controller specify the timing of the pulses, pulse widths, current amplitude, and polarity. FIG. 21 illustrates another embodiment in which a capacitive discharge pulse output circuit 2001 is used to output voltage pulses between stimulation electrodes 1258A and 1258B in accordance with command inputs from the controller 1351. In this embodiment, the command inputs from the controller specify the timing of the pulses, pulse widths, voltage amplitude, and pulse polarity. In order for the controller to specify a voltage amplitude that results in a desired current amplitude for the pulses, the lead impedance may be measured by lead impedance measurement circuit 2002. The output capacitor of the pulse output circuit may then be charged to the appropriate voltage for each pulse. In order to monitor the lead impedance, the controller is programmed to periodically, or upon command from a user via telemetry, charge the output capacitor to a known voltage level, connect the output capacitor to the stimulation leads to deliver a stimulation pulse, and measure the time it takes for the capacitor voltage to decay by a certain amount (e.g., to half of the initial value). In order to minimize patient discomfort, the lead impedance procedure should be performed using as low a voltage as possible. In one embodiment, the controller is programmed to use a first voltage amplitude (e.g., 1 volt) and then compare the measurement count (i.e., the capacitor decay time) to a specified minimum value CntZMin. If the measurement count is below CntZMin, the current delivered during the test is deemed too small for the measurement to be accurate. A second measurement pulse is then delivered at a higher second voltage (e.g., 2 volts). If that count is again below CntZMin, a third measurement pulse is delivered at a still higher third voltage (e.g., 4 volts). With a typical stimulation lead, this procedure limits the measurement current to between roughly 1 mA and 0.6 mA.

Figure 18:
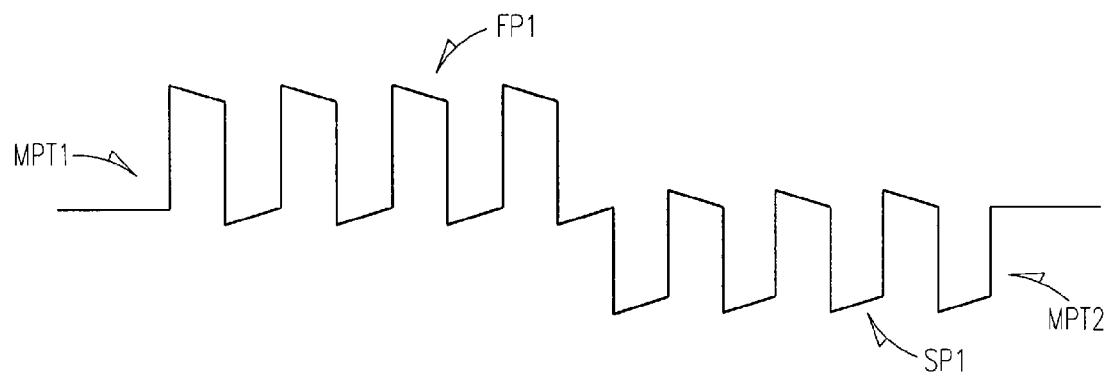
FIG. 18 illustrates a waveform made up of monophasic pulse trains with alternating polarity as would be generated by a capacitive discharge pulse output circuit.
Figure 19:
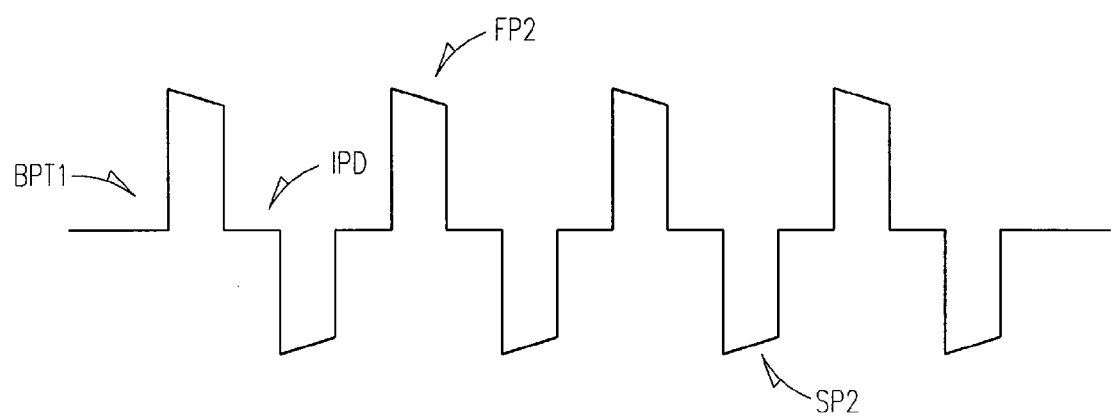
FIG. 19 illustrates a biphasic waveform with alternating polarity as would be generated by a capacitive discharge pulse output circuit.

FIGS. 18 and 19 show example waveforms as would be produced by the capacitive discharge pulse output circuit, which correspond to the waveforms of FIGS. 16 and 17, respectively. With a capacitive discharge pulse output circuit, the voltage amplitude of each pulse is not constant as is the case with a current source pulse output circuit. FIGS. 18 and 19 thus show pulses in which the voltage rises to an initial value and then decays as the output capacitor discharges. Also, the circuitry may incorporate a passive recharge between monophasic pulses in order to dissipate afterpotentials from the stimulation electrodes. FIG. 18 shows such passive recharge cycles where the output circuitry is switched in a manner that causes the voltage between pulses overshoots slightly in a direction opposite to the pulses and decays to zero as the afterpotentials between the stimulation electrodes discharge. Passive recharge is not needed in the case of biphasic pulses as each pulse discharges the afterpotential produced by the preceding pulse. FIG. 19 shows an interphase delay IPD between biphasic pulses. In certain embodiments, it may be desirable to minimize or even eliminate this delay.

In another embodiment, with either a biphasic pulse train or a series of monophasic pulse trains having alternating polarities, the stimulation parameters for the first and second phases may be adjusted separately. For example, the pulse widths and amplitudes for the first and second phases of a biphasic pulse train may be selected to be the same or different. In the case of a series of monophasic pulse trains having alternating polarities, the pulse width, pulse amplitude, duty cycle, and frequency for each of the first and second phases may be selected to be the same or different.

In another embodiment, advantage is taken of an empirical finding that stimulation of the vagus nerve with pulses of different polarities can have different effects. It has been found that vagal stimulation with alternating polarities, delivered as either a biphasic pulse train or by monophasic pulse trains with alternating polarities, results not only in the desired therapeutic effect for preventing or reversing cardiac remodeling as described above, but also with a reduction of undesired side effects. Such side effects from vagal stimulation may include, for example, hoarseness and coughing due to vagal innervation of the larynx. In order to achieve an optimum balance between therapeutic effects and undesired side effects, a neural stimulation waveform with alternating polarities may be applied over time while varying the pulse amplitudes and pulse widths for each polarity. As the pulse amplitudes and widths are varied, a clinical determination may be made as to the therapeutic benefit provided and the extent of any undesired side effects. For example, a biphasic pulse train or a series monophasic pulse trains with alternating polarities may be applied in which the pulse amplitude and pulse width for one polarity are titrated to a therapeutic dose. The pulse amplitude and pulse width for the opposite polarity are then adjusted to control the presence of side-effects. Which one of the two polarities of the pulse train is responsible for producing therapeutic benefits and which polarity is responsible for reducing side effects may be determined empirically. Such a titration procedure may be performed by a clinician after implantation of the device, where the stimulation parameters such as pulse width and amplitude are adjusted via telemetry. The device could also be configured to automatically titrate the therapeutic dose to a target amplitude within a specified period of time. For example, such a titration could be performed rapidly during the first 1-2 weeks after an MI, which has been shown in pre-clinical studies to be the time where the greatest therapeutic benefit is achieved.

Figure 22:
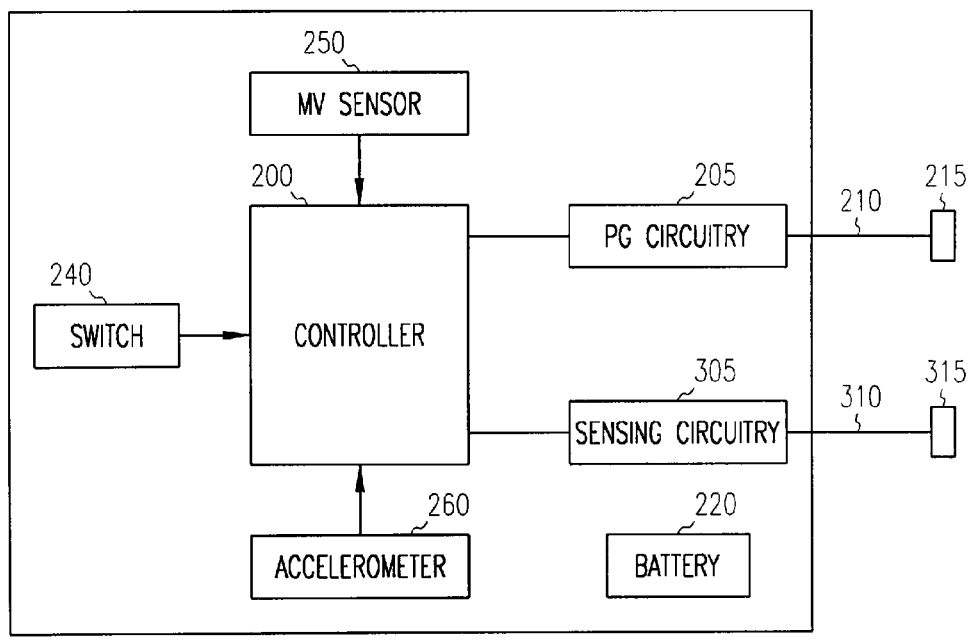
FIG. 22 is a system diagram of an exemplary neural stimulator.

FIG. 22 is a system diagram of an exemplary neural stimulator. A battery 220 provides power to the electronic circuit components of the device. A programmable electronic controller 200 is interfaced to pulse generation circuitry 205 and controls the output of neural stimulation pulses. The controller may also be interfaced to sensing circuitry for sensing cardiac activity or other physiological variables. The controller 200 may be made up of a microprocessor communicating with a memory, where the memory may comprise a ROM (read-only memory) for program storage and a RAM (random-access memory) for data storage. The controller could also be implemented by other types of logic circuitry (e.g., discrete components or programmable logic arrays) using a state machine type of design. The controller includes circuitry for generating clock signals used to keep track of lapsed time intervals and deliver neural stimulation in accordance with a defined schedule. The pulse generation circuitry 205 may be similar to that used in cardiac pacemakers or to that described with reference to FIGS. 21 and 22. The pulse generation circuitry delivers electrical stimulation pulses to a neural stimulation electrode 215 (or electrodes in the case of a bipolar lead) via the lead 210. The neural stimulation electrode may be, for example, a cuff or transvascular electrode that may be disposed for stimulating the vagus nerve or a baroreceptor. A magnetically or tactilely actuated switch 240 interfaced to the controller 200 allows the patient to initiate and/or stop the delivery of neural stimulation pulses. Once begun, the neural stimulation pulses may continue to be delivered for a predetermined length of time or according to a predetermined schedule. The pulse frequency, pulse width, pulse amplitude, pulse polarity, and bipolar/unipolar stimulation configuration in this embodiment are programmable parameters, the optimal settings of which depend upon the stimulation site and type of stimulation electrode. The device may also be equipped with different sensing modalities for sensing physiological variables affected by neural stimulation. The device may then be programmed to use these variables in controlling the delivery of neural stimulation. The device in FIG. 22 includes sensing circuitry 305 connected to an electrode 315 (or electrodes in the case of a bipolar lead) via the lead 310 which may be intravenously disposed in the heart for detecting cardiac electrical activity. The sensing circuitry 305 allows the device to measure heart rate and to compute parameters derived therefrom such as heart rate variability or heart rate turbulence for use in controlling the delivery of neural stimulation. Separate sensing channels may be provided for detecting both atrial and ventricular beats. For example, vagal stimulation slows the heart rate, and the device may be programmed to titrate the level of neural stimulation delivered in response to a detected change in heart rate. As neural stimulation may also affect respiratory rate, the device also includes a minute ventilation sensor 250 and may be programmed to similarly titrate the level of neural stimulation delivered in response to a detected change in respiratory rate. An accelerometer 260 is also interfaced to the controller which enables the device to detect heart sounds, the intensity of which may be reflective of myocardial contractility. A pressure sensor could also be used for this purpose. The accelerometer 260 may also be used to detect coughing brought about by vagal stimulation. The device may then be programmed so that neural stimulation is decreased or stopped if persistent coughing by the patient is detected.

One of ordinary skill in the art will understand that, the modules and other circuitry shown and described herein can be implemented using software, hardware, and combinations of software and hardware. As such, the term module is intended to encompass software implementations, hardware implementations, and software and hardware implementations.

The methods illustrated in this disclosure are not intended to be exclusive of other methods within the scope of the present subject matter. Those of ordinary skill in the art will understand, upon reading and comprehending this disclosure, other methods within the scope of the present subject matter.

The above-identified embodiments, and portions of the illustrated embodiments, are not necessarily mutually exclusive. These embodiments, or portions thereof, can be combined. For example, various embodiments combine two or more of the illustrated processes. In various embodiments, the methods provided above are implemented as a computer data signal embodied in a carrier wave or propagated signal, that represents a sequence of instructions which, when executed by a processor cause the processor to perform the respective method. In various embodiments, methods provided above are implemented as a set of instructions contained on a computer-accessible medium capable of directing a processor to perform the respective method. In various embodiments, the medium is a magnetic medium, an electronic medium, or an optical medium.

Although specific embodiments have been illustrated and described herein, it will be appreciated by those of ordinary skill in the art that any arrangement which is calculated to achieve the same purpose may be substituted for the specific embodiment shown. This application is intended to cover adaptations or variations of the present subject matter. It is to be understood that the above description is intended to be illustrative, and not restrictive. Combinations of the above embodiments as well as combinations of portions of the above embodiments in other embodiments will be apparent to those of skill in the art upon reviewing the above description. The scope of the present subject matter should be determined with reference to the appended claims, along with the full scope of equivalents to which such claims are entitled.

What is claimed is:

1. An implantable device, comprising:
   stimulation circuitry for delivering electrical stimulation to one or more electrodes adapted for disposition to stimulate the heart and vagus nerve;
   a controller connected to the stimulation circuitry for controlling the delivery of electrical stimulation by the stimulation circuitry;
   an accelerometer interfaced to the controller;
   wherein the controller is configured to operate the stimulation circuitry so as to deliver both cardiac pacing pulses and neural stimulation pulses to the one or more electrodes; and,
   wherein the controller is configured to decrease or cease delivery of neural stimulation pulses if coughing is detected from accelerometer signals.

2. The device of claim 1 wherein the controller is configured to deliver the neural stimulation pulses and cardiac pacing pulses as a higher frequency neural stimulation signal modulated on a lower frequency cardiac pacing signal.

3. The device of claim 1 wherein the controller is configured to deliver cardiac pacing pulses alternated with neural stimulation pulses.

4. The device of claim 1 wherein the controller is configured so that the stimulation circuitry delivers neural stimulation pulses as a biphasic pulse train with alternating polarities.

5. The device of claim 1 wherein the controller is configured so that the stimulation circuitry delivers neural stimulation pulses as a series of monophasic pulse trains where the polarity of each consecutive pulse train alternates.

6. The device of claim 1 wherein the controller is configured to deliver neural stimulation pulses continuously.

7. The device of claim 1 wherein the controller is configured to deliver neural stimulation pulses intermittently for specified periods of time.

8. The device of claim 1 wherein the controller is configured to deliver neural stimulation pulses intermittently with a duty cycle of 10 seconds ON and 50 seconds OFF.

9. The device of claim 1 wherein the stimulation circuitry further comprises a current source pulse output circuit for outputting neural stimulation pulses at a current amplitude specified by the controller.

10. The device of claim 1 wherein the stimulation circuitry further comprises a capacitive discharge pulse output circuit and a lead impedance measurement circuit for outputting pulses at a current amplitude specified by the controller.

11. The device of claim 1 wherein the controller is configured so that the stimulation circuitry delivers neural stimulation pulses as a series of monophasic pulse trains where the polarity of each consecutive pulse train alternates with first and second phases and further wherein the pulse width, pulse amplitude, duty cycle, and frequency for each of the first and second phases are separately adjustable.

12. The device of claim 11 wherein the controller is programmed such that the first phase is titrated to achieve a desired therapeutic benefit and the second phase is titrated to achieve a desired reduction in side effects.

* * * * *